United States Patent [19]

Shull et al.

[11] Patent Number: 5,932,709

[45] Date of Patent: Aug. 3, 1999

[54] PROCESS FOR PREPARING GLYCOSYLATED ANALOGS OF CAMPTOTHECIN

[75] Inventors: Brian Keith Shull, Ann Arbor, Mich.; Clarke Slemon, Willowdale, Canada; Masato Koreeda, Ann Arbor, Mich.

[73] Assignee: University of Michigan, Mich.

[21] Appl. No.: 08/876,824

[22] Filed: Jun. 16, 1997

Related U.S. Application Data

[62] Division of application No. 08/429,941, Apr. 27, 1995, Pat. No. 5,677,286.

[51] Int. Cl.$^6$ ...................................................... C07H 1/00
[52] U.S. Cl. .......................... 536/18.6; 536/4.1; 536/17.2; 536/17.9; 536/18.1; 536/18.5
[58] Field of Search .................................. 536/18.5, 18.6, 536/17.9, 4.1, 17.2, 18.1

[56] References Cited

U.S. PATENT DOCUMENTS 5,446,047   8/1995   Danislefsky et al. .................... 514/280

*Primary Examiner*—Elli Peselev
*Attorney, Agent, or Firm*—Medlen & Carroll, LLP

[57] ABSTRACT

The present invention relates to chemotherapeutic agents, and more particularly, to novel analogs of camptothecin. The camptothecin analogs display increased solubility through the hydrophilicity of added non-ionic sugar substituents. In accordance with the present invention, a member from the class of novel camptothecin analogs is to be delivered in vivo as a chemotherapeutic agent to fight cancer growth in the body.

25 Claims, 5 Drawing Sheets

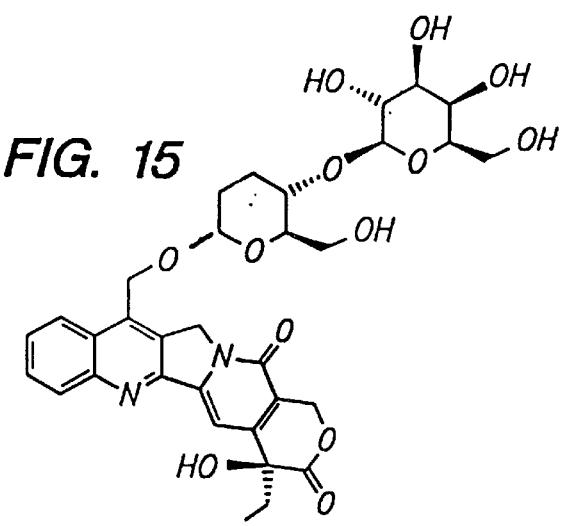
FIG. 15
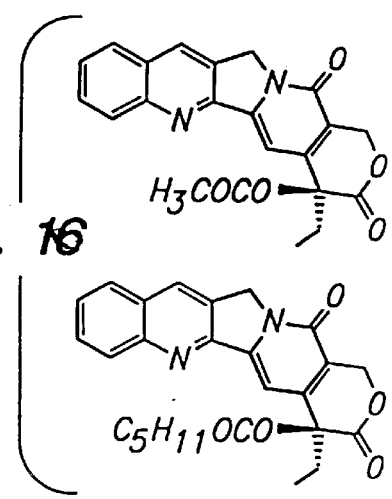
FIG. 16
FIG. 17
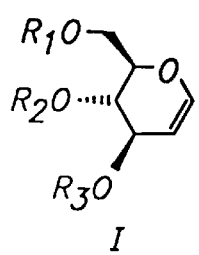
I
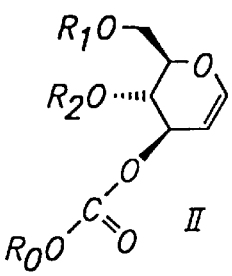
II
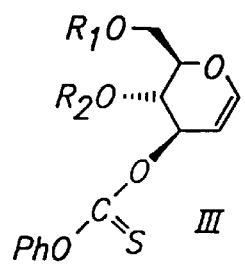
III
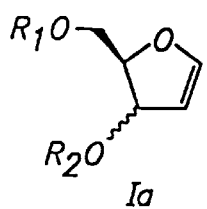
Ia
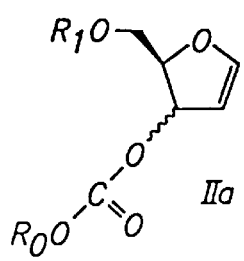
IIa
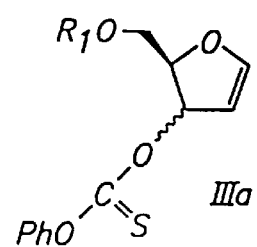
IIIa
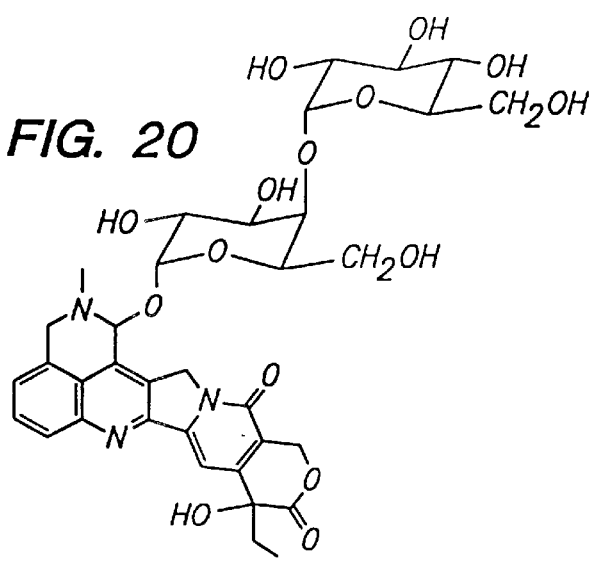
FIG. 20

PROCESS FOR PREPARING GLYCOSYLATED ANALOGS OF CAMPTOTHECIN

The present application is a divisional of U.S. patent application Ser. No. 08/429,941, filed Apr. 27, 1995, now U.S. Pat. No. 5,677,286, issued Oct. 4, 1997.

FIELD OF THE INVENTION

The present invention relates to chemotherapeutic agents, and more particularly, to novel analogs of camptothecin.

BACKGROUND OF THE INVENTION

Despite the enormous efforts and resources directed at finding a cure, cancer remains an elusive and deadly foe for mankind. The standard methods of treatment usually include chemotherapy, radiation treatment, and surgical removal or tumors and/or growths, or some combination thereof. These treatments, combined with an emphasis on preventative lifestyle modification, have afforded a measure of success in the battle against some cancers. However, cancer remains one of the leading causes of mortality, and cancers detected at matured stages are invariably fatal.

Numerous chemical agents have been devised for the treatment of cancer with varying degrees of efficacy. However, no single drug has one hundred percent effectiveness against different cancers, and negative side-effects ranging from minor to serious are always present.

Recently, there has been much research directed toward the use of camptothecin and its derivatives to fight cancer. Isolated in 1966 from the Chinese tree *Camptotheca acuminata,* camptothecin was found to have significant efficacy in animal tumor models. Upon advancement to human clinical studies, camptothecin was found to have mixed results in fighting tumor growth and possessed side effects ranging from vomiting and diarrhea to myelosuppression and hemorrhagic cystitis. The side effects were so severe that Phase II clinical trials were eventually discontinued in the United States.

It is believed that camptothecin has a unique mechanism of action, i.e., via topoisomerase I DNA damage by binding and stabilizing a covalent DNA-topoisomerase I complex in which one of the DNA strands is broken. [See Slichenmyer et al., "The Current Status Of Camptothecin Analogues As Antitumor Agents," J. Nat'l. Cancer Inst. 85:2 (1993) and references cited therein]. Among the formidable challenges facing any effort to develop the potential anticancer properties of camptothecin into a useable treatment are clearly the problems of drug delivery and toxicity.

Drug delivery is complicated by the fact that camptothecin is water-insoluble in its unmodified state. To this end several derivatives of camptothecin have been developed in order to address those two problems. In 1991, Kingsbury et al. [see "Synthesis Of Water-Soluble (Aminoalkyl) camptothecin Analogues: Inhibition Of Topoisomerase I And Antitumor Activity," J. Med. Chem. 34:98(1991)] described the synthesis of several water-soluble analogs of camptothecin, by introduction of aminoalkyl groups into the camptothecin ring system. One of these analogs in particular, [(s)-9-dimethylaminomethyl-10-hydroxycamptothecin hydrochloride], later referred to as topotecan or TPT, was found to have significant anti-tumor effects when tested against various carcinoma cells in an in vitro clongenic assay. In animal studies, TPT was found to be at least as good or better than camptothecin in its effectiveness against tumor growth for a variety of cancers.

In human clinical studies, TPT was found to be clearly more promising than camptothecin in its efficacy. However, the derivative still caused several significant side effects, including myelosuppression, neutropenia, and thrombocytopenia.

Sawada et al. [see "Synthesis And Antitumor Activity Of 20(S)-Camptothecin Derivatives: Carbamate-Linked, Water Soluble Derivatives Of 7-Ethyl-10-hydroxycamptothecin," Chem. Pharm. Bull 39:1446 (1991)] prepared several derivatives of camptothecin by bonding the phenolic hydroxyl group of 7-ethyl-10-hydroxycamptothecin with diamines through a monocarbamate linkage. These diamine derivatives were made water-soluble by conversion to their hydrochloride salts. One derivative in particular, 7-ethyl-10-[4-(piperidino)-1 -piperidino]carboxylcamptothecin hydrochloride ("CPT-11"), possessed significant in vivo preclinical activity; it exhibited negligible in vitro activity as shown by its inability to inhibit Topoisomerase I activity [see Kingsbury et al. supra] and tumor cell growth [see Kingsbury et al. supra and Kawato et al., "Intracellular Roles Of SN-38, A Metabolite Of The Camptothecin Derivative CPT-11, In The Antitumor Effect Of CPT-11," Cancer Res. 51:4187 (1991)], due to the fact that CPT-11 must first be metabolized by the body into its bioreactive form SN-38; thus making CPT-11 a "pro-drug." In fact, the in vivo preclinical anti-cancer effects of CPT-11 were more significant and wider ranging than either camptothecin or any other analog synthesized to date.

However, the promising effects of CPT-11 were still accompanied by significant side effects when the studies progressed to human clinical trials. Although the broad range of side effects was not generally present for CPT-11, severe respiratory complications combined with constant diarrhea pose significant challenges for CPT-11 based chemotherapy. [See Slichenmeyer et al. supra].

Clearly, there remains a need for a powerful anti-cancer derivative of camptothecin which does not possess significant side effects in humans undergoing treatment with such derivatives.

SUMMARY OF THE INVENTION

The present invention relates to chemotherapeutic agents, and more particularly, to novel analogs of camptothecin. A camptothecin "derivative" or "analog" of the present invention has the fundamental structure of unmodified camptothecin (see FIG. 1). The contemplated camptothecin analogs possess the substructure of unmodified camptothecin substituted with either one or two side chains or one optionally substituted, fused, carbocyclic or heterocyclic ring and one side chain wherein the side chains or ring substituents are independently selected from: lower alkyl, lower alkenyl, lower alkoxy, lower alkylamino, di-lower alkylamino, lower alkoxy-lower alkyl, lower alkylamino-lower alkyl, or dilower alkylamino-lower alkyl; and where one or two hydroxyls are attached at any of the methyl or methylene carbons of these appended chains or rings; and wherein further at least one of these primary or secondary alcohols is glycosylated with a saccharide substituent which may be exemplified by but is not limited to 2,3-desoxy-2,3-dehydroglucose, 2,3-desoxy-2,3-dehydroglucose diacetate, glucoside, glucoside tetraacetate, mannoside, mannoside tetraacetate, galactoside, galactoside tetraacetate, alloside, alloside tetraacetate, guloside, guloside tetraacetate, idoside, idoside tetraacetate, taloside, taloside tetraacetate, rhamnoside, rhamnoside triacetate, maltoside, maltoside heptaacetate, 2,3-desoxy-2,3-dehydromaltoside, 2,3- desoxy-2,3-dehydromaltoside pentaacetate, 2,3-desoxymaltoside, lactoside, lactoside tetraacetate, 2,3-desoxy-2,3-dehydrolactoside, 2,3-desoxy-2,3-dehydrolactoside pentaacetate, 2,3-desoxylactoside, glucouronate, N-acetylglucosamine. In one embodiment, the present invention contemplates a camptothecin analog modified at the seven position by chemical, enzymatic, or biological means, such that it contains carbohydrate moieties. (See e.g., FIGS. 4–15).

The embodiments of the present invention contemplate the camptothecin basic skeleton glycosylated by a wide variety of sugar moieties. The sugar moieties are connected to the basic camptothecin skeleton by linker side chains or rings containing primary or secondary alcohols. Camptothecin having such linker side-chains or rings (in preparation for the addition of sugar moieties) are referred to as "modified camptothecins". The molecular architecture unites the camptothecin substructure, which carries the anti-cancer activity, with the sugar substructure, which confers the hydrophilic-lipophilic balance. The combination is achieved to allow both sufficient durability to enable drug transport and delivery and sufficient flexibility so that the camptothecin subgroup may (if necessary) be disconnected by enzymatic and/or hydrolytic mechanisms. While not intending to limit the invention to any particular mechanism, it is believed that the linker and the sugar together perturb the crystal lattice of the camptothecin analog so as to remove the high crystal binding forces which make many camptothecin-like substances highly insoluble not just in water but in practically all solvents.

The attempted solubilization of camptothecin-like molecules is not new. In the prior art however this solubilization is achieved principally through the use of salts of basic amino groups which are attached either directly or indirectly to the camptothecin skeleton. In contrast, the present invention contemplates increasing solubilization through the hydrophilicity of non-ionic sugar substituents. Although a minority of structures which fall within the scope of this invention do contain basic nitrogens these are either part of the sugar or simply constitute a part of the linker unit.

Camptothecin glycosides have been previously described, for example one is a natural product called chaboside [see Tetrahedron Lett. 31:5169 (1990) and "10-Hydroxycamptothecin Glycosides as Antitumor Agents" JP 63238098] The glycosides heretofore described, however, have the sugar moiety directly bonded through a simple oxygen to the camptothecin substructure (FIG. 1). These phenolic glycosidic links are readily hydrolyzable. Consequently these prior art molecules lack the durability of the analogs of the present invention.

A wide variety of sugar units indirectly linked to the camptothecin substructure are contemplated. The modes of preparation of alcohol-sugar glycoside linkages are well known to practitioners of the art as is evidenced by the comprehensive reviews addressing this particular type of bond formation [see K. Toshima and K. Tatsuta, "Recent progress in O-glycosylation methods and its application to natural products synthesis" Chem. Rev. 1503 (1993); R. R. Schmidt "New methods for the synthesis of glycosides and oligosaccharides-Are there alternatives to the Koenigs-Knorr method?" Angew. Chem. Int. Ed. Engl. 25:212 (1986); and N. K. Kochetkov "Recent developments in the synthesis of polysaccharides and stereospecificity of the glycosylation reactions," Stud. Nat. Prod. Chem. 14:201 (1994)]. The glycosidic bonds required in the present invention are prepared using these glycosylation techniques either on the modified camptothecin itself or on the more soluble C-20 hexanoate whose synthesis is described herein in the experimental section. The hexanoate solubilizing group may be easily removed, for example during the deprotection of the sugar protecting groups. The present invention contemplates molecules containing the camptothecin substructure which when glycosylated produce the camptothecin glycoside analog of the present invention. The corresponding aglycons are either already described in the chemical literature or are easily synthesized by standard reactions from substances whose preparation is already described in the chemical literature. Examples of previously described compounds which fall within the scope of the present invention when glycosylated include 5-hydroxymethylcamptothecins; 5,5-Bis(hydroxymethyl)camptothecin; 7-[N,N-(2-hydroxyethyl)aminomethyl]-10,11-ethylenedioxycamptothecin; 7-[N-methyl-N-(2-hydroxyethyl)aminomethyl]-10,11-ethylenedioxycamptothecin; 7-[N-methyl-N-(2-hydroxyethyl)aminomethyl]-10,11-methylenedioxycamptothecin. Examples of previously described compounds which are readily converted into new camptothecin analogs include 7-chlorocamptothecin, 9-bromocamptothecin, 9-chlorocamptothecin, 10-bromocamptothecin, 10-chlorocamptothecin, 11-bromocamptothecin, 11-chlorocamptothecin, 12-bromocamptothecin, and 12-chlorocamptothecin. Other compounds within the scope of this invention which are also contemplated are 10-(2-hydroxyethoxy)camptothecin, and 10-[2,3-dihydroxy-propoxy]camptothecin.

In one embodiment, the present invention contemplates an analog that is glycosylated on a 7-position side-chain. One embodiment of the present invention contemplates a camptothecin that is substituted at the 7 position by a lower alkyl group functionalized at a primary or secondary carbon by a hydroxyl through which is connected a sugar. All may be optionally substituted in the 10,11 positions with either a methylenedioxy or ethylenedioxy ring. One embodiment of the present invention contemplates glycosylation of the modified camptothecin, 7-hydroxymethylcamptothecin. The synthesis of the corresponding aglycons may be facilitated by using the C-20 hexanoate of camptothecin as an alternate substrate or by manipulation of the opened lactone form followed by subsequent reclosure. In another embodiment, the present invention contemplates an analog having a linker at the 7 position that allows for glycosylation. While not limited to particular linkers, a preferred linker is oxymethyl. One analog of the present invention is 7-[4,6-di-O-acetyl-2,3-dideoxy-α-D-erythro-hex-2-enopyranosyl]-oxymethylcamptothecin. Another analog of the present invention is 7-[6-O-acetyl-4-O-(2,3,4,6-tetra-O-acetyl-α-D-glucopyranosyl)-2,3-dideoxy-α-D-erythro-hex-2-enopyranosyl]-oxymethylcamptothecin. Another analog of the present invention is 7-[4-O-(α-D-glucopyranosyl)-2,3-dideoxy-α-D-erythro-hex-2-enopyranosyl]-oxymethylcamptothecin. Another analog of the present invention is 7-[2,3-dideoxy-α-D-erythro-hex-2-enopyranosyl camptothecin. Another analog of the present invention is 7-[6-O-acetyl-4-O-(2,3,4,6-tetra-O-acetyl-β-D-galactopyranosyl)-2,3-dideoxy-α-D-erythro-hex-2-enopyranosyl]-oxymethylcamptothecin. Another analog of the present invention is 7-[4-O-(β-D-galactopyranosyl)-2,3-dideoxy-α-D-erythro-hex-2-enopyranosyl]-oxymethylcamptothecin. Another analog of the present invention is 7-[4,6-di-O-acetyl-2,3-dideoxy-α-D-erythro-hexanopyranosyl]-oxymethylcamptothecin. Another analog of the present invention is 7-[2,3 dideoxy-α-D-erythro-hexanopyranosyl]-oxymethylcamptothecin. Another analog of the present invention is 7-[6-O-acetyl-4-O-(2,3,4,6-tetra-O-acetyl-α-D-glucopyranosyl)-2,3-dideoxy-α-D-erythro-hexanopyranosyl]-oxymethylcamptothecin. Another analog of the present invention is 7-[4-O-(α-D-glucopyranosyl)-2,3-dideoxy-α-D-erythro-hexanopyranosyl]-oxymethylcamptothecin. Another analog of the present invention is 7-[6-O-acetyl-4-O-(2,3,4,6-tetra-O-acetyl-β-D-galactopyranosyl)-2,3-dideoxy-α-D-erythro-hexanopyranosyl]-oxymethylcamptothecin. Yet another analog of the present invention is 7-[4-O-(β-D-galactopyranosyl)-2,3-dideoxy-α-D-erythro-hexanopyranosyl]-oxymethylcamptothecin.

In one embodiment, an analog of the present invention is synthesized by a) providing in any order: i) unmodified camptothecin, ii) a modifying reagent, iii) a derivatizing reagent, and iv) a catalyst; b) reacting in any order: i) unmodified camptothecin and ii) a modifying reagent to form a modified camptothecin; c) reacting in any order: i) the modified camptothecin of step (b), ii) a derivatizing reagent, and iii) a catalyst to form a chemotherapeutic anti-cancer analog of the camptothecin molecule of FIG. 1.

Modifying reagents are those reagents which will act on unmodified camptothecin to add a side-chain, for example oxymethyl. In one embodiment, the modifying reagent is an alcohol (e.g., methanol). Derivatizing reagents are those reagents which provide the substituents added to modified camptothecin. In one embodiment, the derivatizing reagent is a carbohydrate glycal. In one embodiment the carbohydrate glycal is selected from the group consisting of glucose glycal (glucal), maltose glycal (maltal), and lactose glycal (lactal). A catalyst, in general, is a substance which increases the rate of a chemical reaction. In this particular reaction, a catalyst is a substance which increases the rate of formation of the glycosylated camptothecin analog. In one embodiment, the catalyst is a molecular diatomic halogen. In one embodiment, the molecular diatomic halogen is molecular diatomic iodine.

In one embodiment, the carbohydrate glycal is a disaccharide glycal, for example maltose glycal (maltal), and is synthesized by a) providing in any order: i) unmodified disaccharide, ii) a protecting reagent, iii) a disaccharide derivatizing reagent, and iv) a reducing agent; b) reacting in any order: i) unmodified disaccharide and ii) a protecting reagent to form a protected disaccharide; c) reacting in any order: i) the protected disaccharide of step (b) and ii) a disaccharide derivatizing reagent to form a derivatized protected disaccharide; d) reacting in any order: i) the derivatized protected disaccharide of step (c) and ii) an reducing agent to form a disaccharide glycal. In one embodiment the unmodified disaccharide is maltose. In another embodiment the unmodified disaccharide is lactose. Protecting reagents are those reagents which protect particular functionalities of the disaccharide from being destroyed in subsequent reactions. In one embodiment the protecting reagent is an esterifying reagent, for example acetic anhydride. Disaccharide derivatizing agents are those reagents which convert a disaccharide into a disaccharide halide. In one embodiment, the disaccharide derivatizing reagent is a halogenating reagent, for example hydrobromic acid. In one embodiment, the reducing agent is Zn/CuSO$_4$.

In one embodiment, the activated carbohydrate glycal is an activated disaccharide glycal. Activated disaccharide glycals are those glycals which have sufficient reactivity to readily react with modified camptothecins to form glycosylated camptothecin analogs in high yields (as compared to yields with unactivated disaccharide glycals), for example pentaacetylbenzoyl glycal, and are synthesized by a) providing in any order: i) disaccharide glycal, ii) an activating reagent, and iii) a catalyst; b) reacting in any order: i) the disaccharide glycal, ii) a protecting reagent, and iii) a catalyst to form an activated disaccharide glycal. In one embodiment the disaccharide glycal is maltal. Activating reagents are those reagents that convert disaccharide glycals into activated disaccharide glycals. In one embodiment the activating reagent is a carboxylic acid, for example o-anisic acid. In this particular reaction a catalyst is a substance which increases the rate of formation of the activated disaccharide glycal. In one embodiment, the catalyst is a molecular diatomic halogen. In one embodiment, the molecular diatomic halogen is molecular diatomic iodine.

In one embodiment, the present invention contemplates a method of synthesizing a chemotherapeutic anti-cancer glycosylated analog of the camptothecin molecule of FIG. 1, comprising the steps: a) providing a modified camptothecin; b) synthesizing a disaccharide glycal; c) treating said disaccharide glycal so as to generate an activated disaccharide glycal; and d) reacting in any order: i) said modified camptothecin of step (a), ii) said activated disaccharide glycal of step (c), and iii) a catalyst, under conditions so as to form a chemotherapeutic anti-cancer analog of the camptothecin molecule of FIG. 1. In one embodiment, the modified camptothecin of step (a) is prepared by reacting unmodified camptothecin with methanol and molecular diatomic iodine to form a modified camptothecin. In one embodiment, the disaccharide glycal of step (b) is synthesized according to the following procedure: 1) providing in any order: i) unmodified disaccharide, ii) acetic anhydride, iii) hydrobromic acid, and iv) zinc/cuprous sulfate; 2) reacting said unmodified disaccharide with said acetic anhydride to form a protected disaccharide; 3) reacting said protected disaccharide of step (2) with said hydrobromic acid to form a derivatized protected disaccharide; and 4) reacting said derivatized protected disaccharide of step (3) with said zinc/cuprous sulfate to form a disaccharide glycal. In one embodiment, the treating in step (c) comprises reacting in any order: i) said disaccharide glycal, ii) o-anisic acid, and iii) molecular diatomic iodine to form an activated disaccharide glycal. In one embodiment, said catalyst is a molecular diatomic halogen, for example molecular diatomic iodine.

It should be clear that the order of the steps is, in some instances, variable. For example, while the synthesis of the disaccharide glycal must precede the treating step creating the activated disaccharide glycal, the preparation of the modified camptothecin is independent of the creation of the activated disaccharide glycal (i.e., it may be done before, during, or after the synthesis of the activated disaccharide glycal) and the only temporal requirement is that the activated disaccharide glycal and the modified camptothecin are prepared before their eventual reaction (in step (d)) to form the glycosylated camptothecin analog of the present invention.

The analogs of the present invention have numerous uses. First, they may be successfully employed as standards for analytical techniques (e.g., HPLC) so that new analogs can be easily identified. In addition, the present invention also contemplates in vivo use; in accordance with the present invention, a member from the class of novel camptothecin analogs is to be delivered as a chemotherapeutic agent to fight cancer growth in the body.

DESCRIPTION OF THE DRAWINGS

FIG. 15 shows the structure of a preferred camptothecin analog of the present invention, 7-[4-O-(β-D-galactopyranosyl)-2,3-dideoxy-α-D-erythro-hexanopyranosyl-oxymethylcamptothecin.

FIG. 16 shows the structure of two prior art camptothecin analogs altered at the 20 position.

FIG. 17 shows the structure of preferred glycosylation reaction glycals of the formulas I-III and Ia-IIIa.

FIG. 20 shows the structure of a camptothecin analog of the present invention, 9-ethyl-1-[(4-O-α-D-glucopyranosyl-α-D-galactopyranosyl)oxy]-1,2,3,9,12,15-hexahydro-9-hydroxy-2-methyl-10H,13H-Benzo[ij]pyrano [3',4':6,7]indolizino[1,2-c][2,6]naphthyridine-10,13-dione.

DESCRIPTION OF THE INVENTION

Figure 1:
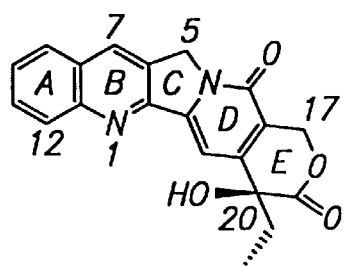
FIG. 1 is a structure of unmodified camptothecin.
Figure 2:
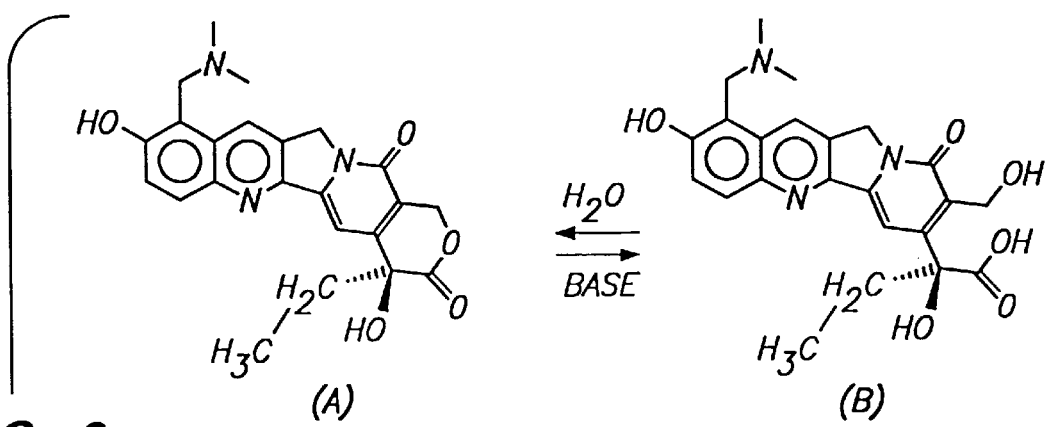
FIG. 2 shows the structure of [(s)-9-dimethylaminomethyl-10-hydroxy-camptothecin-hydrochloride] (topotecan or TPT) a previously described camptothecin derivative of the prior art (A), its lactone ring opened form (B), and the structure of 7-ethyl-10-[4-(piperidino)-1-piperidino]carboxylcamptothecin hydrochloride (CPT-11) another previously described camptothecin derivative of the prior art (C).

The present invention relates to chemotherapeutic agents, and more particularly, to novel analogs of camptothecin. The description of the present invention involves: (I) Camptothecin and Previously Described Derivatives; (II) Properties of Camptothecin Analogs of the Present Invention; (III) Synthesis of Novel Glycosylated Camptothecin Analogs; (IV) Methodology for Screening Camptothecin Analogs; and (V) In Vivo Uses.

I. Camptothecin And Previously Described Derivatives

A. Physical Properties

Camptothecin in its unmodified form is quite insoluble in water (20 μg/mL). As a result, the sodium salt of camptothecin, which is water soluble, was used in clinical trials, although the anti-cancer efficacy of the sodium salt was much less than unmodified camptothecin.

The two camptothecin derivatives which had received the most interest for their possible anti-cancer effects were CPT-11 and TPT. Both compounds exhibited improvement in the area of solubility, compared to camptothecin. CPT-11, which was administrated as its hydrochloride trihydrate had a water solubility of 32 mg/mL. TPT, which was administered as its hydrochloride salt had a water solubility of 1 mg/mL. [See Kingsbury et al. supra].

B. Biological Properties

Camptothecin was used as a control to test the anti-cancer efficacy of the novel camptothecin analogs of the present invention. Two types of in vitro assays were used to measure the effectiveness of both unmodified camptothecin and the analogs of the present invention: first, the compound of interest was utilized in the well-established topoisomerase I assay, to determine the degree to which the drug inhibited the activity of topoisomerase I; second, the compound of interest was tested to determine the inhibition of cell growth for several different cell lines (HT-29: human colon tumor, MCF-7: human breast tumor, B16: murine melanoma, P388: murine leukemia, P388/CPT: CPT-resistant murine leukemia cells) using the MTT assay.

The in vitro effectiveness of TPT correlates well with its usefulness in vivo. In particular, the topoisomerase I $IC_{50}$ for TPT-HCl was 0.504 μg/mL (1.1 μM, MW=457.9 g/mol). [See Wall et al., "Plant Antitumor Agents. 30. Synthesis And Structure Activity Of Novel Camptothecin Analogs," J. Med. Chem. 36:2689 (1993)]. In side by side in vivo studies TPT was superior to unmodified camptothecin against P388 murine leukemia, Lewis lung carcinoma, and B16 murine melanoma. [See Johnson et al., "Preclinical Profile Of SK And F 104684, A Water-Soluble Analog Of Camptothecin," Presented At The Sixth NCI-EORTC Symposium On New Drugs In Cancer Therapy, Amsterdam, March, 1991 and Johnson et al., "Comparative Efficacy Of Topotecan, Irenotecan, Camptothecin And 9-aminocamptothecin In Preclinical Tumor Models," In Proceedings On The Seventh NCI-EORTC Symposium On New Drugs In Cancer Therapy, Amsterdam, 1992, p. 85].

In contrast, the in vitro efficacy for CPT-11 is negligible [see Kingsbury et al. supra and Kawato et al. supra] and belies its in vivo effectiveness. Researchers have believed that the lack of topoisomerase I inhibitory activity of CPT-11 is due to the fact that CPT-11 must be metabolized by the body into a bioreactive form, (SN-38), thus making it a 'pro-drug'.

II. Properties Of Camptothecin Analogs Of The Present Invention

A. Physical Properties

The camptothecin analogs of the present invention have significantly improved water solubility compared to unmodified camptothecin as shown in Table 1. The improved solubility is due to the novel carbohydrate groups attached to the relatively hydrophobic camptothecin ring system. Note that the modified camptothecin analogs of the present invention will be referred hereinafter by their abbreviated codes as follows: HAR4=7-[4,6-di-O-acetyl-2,3-dideoxy-α-D-erythro-hex-2-enopyranosyl] oxymethylcamptothecin; HAR5=7-[6-O-acetyl-4-O-(2,3,4,6-tetra-O-acetyl-α-D-glucopyranosyl)-2,3-dideoxy-α-D-erythro-hex-2-enopyranosyl]oxymethylcamptothecin; HAR6=7-[4-O-(α-D-glucopyranosyl)-2,3-dideoxy-α-D-erythro-hex-2-enopyranosyl]-oxymethylcamptothecin; HAR7=7-[2,3-dideoxy-α-D-erythro-hex-2-enopyranosyl]-oxymethylcamptothecin.

TABLE 1

| Analog | Solubility ($\mu$g/mL) |
| --- | --- |
| HAR4 | 155 |
| HAR5 | 35 |
| HAR6 | 1620 |
| HAR7 | 62 |

In addition to testing for water solubility, one of the analogs of the present invention, HAR7, was tested for solubility in various other solvents and solvent mixtures, to determine the system which provides the greatest solubility for the analog. The results of those solubility experiments are shown below in Table 2:

TABLE 2

| Solvent | Solubility ($\mu$g/ml) |
| --- | --- |
| 5% Ethanol/DSW[1] | 177 |
| 5% Ethanol/Water | 80 |
| 10% Ethanol/Water | 143 |
| 20% Ethanol/Water | 380 |
| Pure Ethanol | 1983 |
| 0.1 M Citrate Buffer | 24 |
| 0.2 M Acetate Buffer | 23 |
| 2 M Acetate Buffer | 29 |
| 0.2 M NaH$_2$PO$_4$ Buffer | 32 |
| 0.2 M Na$_2$HPO$_4$ Buffer | 30 |
| 4:1:5 PG[2]/Ethanol/Water | 740 |
| 4:1:5 PG/Ethanol/Saline | 893 |
| 4:1:5 PG/Ethanol/DSW | 960 |
| PEG 300[3] | >5000 |

Key:
1) DSW.
2) PG:Propylene Glycol.
3) PEG 300:Polyethylene Glycol 300.

III. Synthesis Of Novel Glycosylated Camptothecin Analogs

A recent development in the area of pharmaceutical science has centered around efforts to increase to bioavailability of known drugs by chemical derivatization. [See L. Brown and R. Thomas, Aust. J. Pharm. Sci. 8:1 (1979); Y. H. Ji et al., J. Med. Chem. 33:2264 (1990); V. Stella et al., J. Med. Chem. 35:145 (1992); and Kleeman et al., J. Med. Chem. 35:559 (1992)]. One approach used by researchers is to develop methods of glycosylating a variety of medicinally-important compounds with the objective of increasing aqueous solubility while hopefully enhancing the pharmacological profile of these agents. Such a process could unlock the benefits of a broad array of biologically-active compounds with intrinsically modest hydrophilicity.

The chemistry of glycals is perfectly suited for addressing the above issues. Glycals, cyclic sugar derivatives containing a 1,2-double bond, are indispensable synthetic precursors in the field of carbohydrate chemistry. Though this class of sugars was discovered by Fischer 80 years ago [see E. Fischer and K. Sitzungsber, Preuss. Akad. Wiss. 16:311 (1913)], there has recently been an immense volume of research using these compounds to synthesize complex polysaccharides and glycosylated products.

One reaction in particular, discovered by Ferrier in 1969 [see R. J. Ferrier, J. Chem. Soc. C p. 570 (1969)] which described a reaction which glycals could be attached to various nucleophiles, allowed synthetic chemists to attach carbohydrates to a variety of non-carbohydrate organic molecules. The result compound being an O-glycoside in which a carbohydrate moiety is attached to an oxygen atom of a typically hydrophobic aglycon (aglycon referring to the non carbohydrate molecule) unit. Although similar glycosylation reactions had been accomplished thermally using water, alcohols and phenols [see B. Helferich, Adv. Carbohydrate Chem. 7:209 (1952); R. J. Ferrier, J. Chem Soc. p. 5443 (1964); and R. J. Ferrier et al., J. Chem Soc. p. 3667 (1962)], the Ferrier reaction's use of boron trifluoride etherate greatly expanded the synthetic scope of the reaction.

Despite its synthetic utility, the Ferrier reaction has been less successfully applied to the commercial glycosylation of medicinally useful compounds. Such reactions, preferably performed on a large scale, require the use of Lewis acid catalysts which are more efficient, less toxic, and less destructive toward the aglycon to be glycosylated. For example, since most of these strong Lewis acids spontaneously react with air and moisture, the use of these Lewis acids presents serious problems in their handling, particularly under the large-scale, industrial setting. Another approach to glycosylation that employs a glycal derivative requires the use of expensive metal catalyst whose effects to human health presents serious drawbacks. [See Hacksell, U., Daves, G. D., Jr., J. Org. Chem. 48:2870 (1983)]. For these reasons, the use of the non-toxic, stable catalyst iodine [see U.S. Pat. 5,278,296, hereby incorporated by reference], which is an extremely mild Lewis acid and yet according to the invention retains enough acidity to effect glycosylation, is the preferred reagent.

In one preferred aspect, the invention concerns O-glycoside compounds obtained by reacting either a soft carbon or oxygen nucleophile compound and a glycosylating agent selected from 3-acylated five- and six-membered glycals in the presence of a catalytic amount of iodine (5–50 mol % with 20 mol % being the most representative) to provide a reaction mixture containing the glycosylated product.

The present invention contemplates the preparation of the necessary glycals by the following procedure. First, the desired carbohydrate may be obtained commercially in non-acetylated form and acetylated by reaction with acetic anhydride in acetic acid with a catalytic amount of hydrobromic acid. The acetylated carbohydrate is thereafter converted to an acetylated carbohydrate halide (e.g., bromide, by reaction with hydrobromic acid in acetic acid). The acetylated carbohydrate halide is converted to the acetylated glycal by reaction with Zn/CuSO$_4$. Finally, the acetylated glycal is converted into a more reactive diacetyl benzoyl glycal form by reaction with ortho-anisic acid (2-methoxybenzoic acid). These glycals, which are considered derivatizing agents, are then reacted with a modified form of camptothecin, namely 7-hydroxymethyl camptothecin. This modified form of camptothecin is itself synthesized by the reaction of camptothecin with a modifying reagent of methanol. Alternatively, a commercially available acetylated carbohydrate may be used and thereby obviate the need for the initial reaction step.

For glycosylation, preferred glycals of the formulas I-III and Ia-IIIa are illustrated in FIG. 17, where $R_0$ is a lower alkyl group and $R_1$, $R_2$ and $R_3$ are the same or different and represent an aliphatic acyl group or an aromatic acyl group such as a benzoyl group.

Any of various suitable solvents can be used for the glycosylation reaction of which THF, acetone, diethyl ether, methylene chloride, chloroform, and benzene are preferred. The reaction temperature and time can be varied, e.g., ranging from −78° to room temperature for about 0.5 to 12 hours.

In another preferred aspect, the invention concerns partly and completely deacylated products having enhanced water-solubility, produced by hydrolysis of one or more acyl groups from the acylated product, under per se commonly used conditions for hydrolysis and workup, namely with Zn (OAc)$_2$○2H$_2$O in methanol or ammonia in methanol.

IV. Methodology For Screening Camptothecin Analogs

We claim chemotherapeutic anti-cancer glycosylated analogs of the camptothecin molecule. These compounds will most often be made by the glycosylation of a camptothecin analog. This section outlines procedures whereby a novel glycosylated camptothecin analog can be screened for useful biological activity.

SCREENING PROCEDURE A

Screening Mode A consists of the following biological tests:

Mode I: Determine whether the aglycone unit of the glycosylated camptothecin analog of interest possesses at least one primary or secondary hydroxyl functional group which can be glycosylated with the sugar unit of interest.

Mode II: Determine whether the glycosylated camptothecin analog of interest has equal or better aqueous solubility than unmodified camptothecin (i.e., ≧20 μg/mL).

Mode III: Determine whether the glycosylated camptothecin analog of interest or the corresponding aglycon inhibits Topoisomerase I, thereby halting DNA replication, no less than 10 times worse than unmodified camptothecin (i.e., has a molar IC$_{50}$ no less than 10 times lower than that of unmodified camptothecin) and can be called a topoisomerase inhibitor.

Mode IV: Determine whether the glycosylated camptothecin analog of interest inhibits in vivo carcinoma growth by the use of animal models, and is therefore an in vivo carcinoma growth inhibitor.

Mode V: Determine whether the glycosylated camptothecin analog of interest exhibits animal toxicity equal to or less than unmodified camptothecin.

A new camptothecin analog ("X") can be evaluated for biological activity using the procedure outlined in Table 3.

TABLE 3

Evaluation Of Biological Activities Of Novel Camptothecin Analogs

| Mode | Result | Interpretation/Next Step |
| --- | --- | --- |
| I | +react | Glycosylation of aglycone unit of analog is readily carried out. Perform glycosylation reaction and evaluate in Modes II, III, IV, and V. |
|  | −react | Glycosylation of aglycone unit of analog is not readily carried out and should not be evaluated further. |
| II | +solub | Glycosylated compound is water soluble/Evaluate in Modes III, IV, and V. |
|  | −solub | Glycosylated compound is not water soluble and is not useful as an anti-cancer chemotherapeutic agent. No further evaluation necessary. |
| III | +inhib | Glycosylated compound or its aglycon is a Topoisomerase I inhibitor/Evaluate in Modes IV and V. |
|  | −inhib | Glycosylated compound is not a Topoisomerase I inhibitor. |
| IV | +inhib | Glycosylated compound is an in vivo carcinoma growth inhibitor/Evaluate in Mode V to determine animal toxicity. |
|  | −inhib | Glycosylated compound is not an in vivo carcinoma growth inhibitor and is not useful as an anti-cancer chemotherapeutic agent. |
| V | +toxic | Glycosylated compound exhibits animal toxicity greater than camptothecin and is not usefull as an anti-cancer chemotherapeutic agent. |
|  | −toxic | Glycosylated compound does not exhibit animal toxicity greater than camptothecin and is useful as an anti-cancer chemotherapeutic agent. |

Key: +react = glycosylation reaction possible; −react = glycosylation reaction impossible; +solub = water soluble; −solub = not water soluble; +inhib = process inhibited; −inhib = process not inhibited; +toxic = exhibits greater animal toxicity than camptothecin; and −toxic = exhibits equal or less animal toxicity than camptothecin.

V. In Vivo Uses

The present invention contemplates using therapeutic compositions of soluble camptothecin analogs, and in particular for treatment of cancer. It is not intended that the present invention be limited by the particular nature of the therapeutic preparation. For example, such compositions can be provided together with physiologically tolerable liquid, gel or solid carriers, diluents, adjuvants and excipients. In addition, camptothecin analogs may be used together with other chemotherapeutic agents, including unmodified camptothecin.

With respect to the mode of administration, the camptothecin analogs may be employed for intravenous, intramuscular, intrathecal or topical (including topical ophthalmic) administration. Formulations for such administrations may comprise an effective amount of camptothecin analog in sterile water or physiological saline.

On the other hand, formulations may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions are preferably prepared as injectables, either as liquid solutions or suspensions; solid forms suitable for solution in, or suspension in, liquid prior to injection may also be prepared.

The camptothecin analogs of the present invention are often mixed with diluents or excipients which are compatible and physiologically tolerable. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Options for optimal method of camptothecin analog administration include, but are not limited to: a 30-minute infusion every three weeks, a 30-minute infusion daily×5 every three weeks, a 24-hour infusion every three weeks, a 120-hour infusion every three weeks, and a 72-hour infusion repeated every three weeks.

Likewise, dosage ranges for camptothecin analog treatment include, but are not limited to: 1 to 200 mg/kg/day.

EXPERIMENTAL

The following examples serve to illustrate certain preferred embodiments and aspects of the present invention and are not to be construed as limiting the scope thereof.

In the experimental disclosure which follows, the following abbreviations apply: PBS (phosphate buffered saline); MTT (3-(4,5-dimethylthiazol-2-yl)-2,5-diphenyltetrazolium bromide); EDTA (ethylenedinitrotetraacetic acid disodium salt); HCl (hydrogen chloride); Tris (triphenylphosphine); NaCl (sodium chloride); SDS (sodium dodecyl sulfate); $Na_2S_2O_3$ (sodium thiosulfate); TAE (Tris-Acetate-EDTA); $H_2SO_4$ (sulfuric acid); $FeSO_4$ (ferrous sulfate); $CuSO_4$ (cuprous sulfate); $MgSO_4$ (magnesium sulfate); NaOAc (sodium acetate); DMF (dimethyl formamide); THF (tetrahydrofuran); $NaHCO_3$ (sodium bicarbonate); HBr (hydrogen bromide); KBr (potassium bromide); DMSO (dimethyl sulfoxide); DMSO-$d_6$ (fully deuterated dimethyl sulfoxide); $CHCl_3$ (chloroform); $CDCl_3$ (deuterated chloroform); $NH_3$ (ammonia); IMEM (Iscove's Minimum Essential Medium); IMDM (Iscove's Modified Dulbecco's Medium); D-MEM (Dulbecco's Modified Eagle Medium); HEPES ((N-[2-hydroxyethyl]piperazine-N'-[2-ethanesulfonic acid])); Anti-PPLO (Antibody against Pleuropneumonia-like Organism); pm (parts per million); [α] (specific rotation); μL (microliters); μg (micrograms); mL (milliliters); L (liters); mg (milligrams); g (grams); hr (hours); mM (millimolar); μM (micromolar); nM (nanomolar); N (normal); nm (nanometers); min (minutes); IU (intravenous units); s.c. (subcutaneous); mm (millimeter); MTD (maximally tolerated dosage); i.p. (intraperitoneal); kg (kilograms); δ (chemical shift); J (coupling constant); s (singlet); d (doublet); t (triplet); q (quartet); m (multiplet); vs (very strong); s (strong); m (medium); w (weak); vw (weak); v (variable); mp (melting point); c (optical path length); NMR (Nuclear Magnetic Resonance); IR (Infrared Spectroscopy); MHz (megahertz); Hz (hertz); $cm^{-1}$ (wavenumbers).

EXAMPLE 1

Solubility Determination Of Both Unmodified Camptothecin And Camptothecin Analogs The water solubility of the camptothecin analogs of the present invention were measured in phosphate buffered saline, pH 7.5 (PBS) by a spectrophotometric assay. Approximately 5 mg of test compound was suspended in 1 mL of PBS in a 1.5 mL cryovial. The suspensions were mixed continuously on a Thermolyne vari-mix at room temperature for 24 hr. The suspensions were then centrifuged at 14000×g for 2 minutes to separate the undissolved materials. The supernatant fluids were diluted appropriately with PBS and the ultraviolet spectrums were recorded on a Beckman 640 DU spectrophotometer. For comparison, a standard stock (2 mg/mL in DMSO) solution was prepared for each analog. The ultraviolet spectrum of a 20 of 40 μg/mL standard working solution was measured. The water solubility of each analog was calculated based on the following formula:

$$C_{unknown} = C_{standard} \times (A_{unknown} \times D_{dilution})/A_{standard}$$

where $C_{unknown}$ is the concentration of the unknown solution to be determined; $C_{standard}$ is the concentration of the standard working solution (either 20 or 40 μg/mL); $A_{standard}$ is the absorbance at 350 nm of the standard working solution; $D_{Dilution}$ is the appropriate dilution factor used so that the absorbance of the unknown working solution is within the dynamic range of the UV spectrophotometer (less than 2 absorbance units).

The solubility of HAR7 in various solvents and solvent systems was measured using one of two experimental methods, depending on the conditions and solvents used.

First, an evaporation method was used in which an excess quantity of HAR7 was added to the solvent of choice. The mixture was finely divided using ultrasonic vibration in order to dissolve the material thoroughly. The resulting mixture was filtered and the solution was evaporated to dryness using a rotary evaporator.

Second, a spectrophotometric method was used in which an excess quantity of HAR7 was added to the solvent of choice. The mixture was finely divided using ultrasonic vibration in order to dissolve the maximum amount of solid. The resulting suspension was filtered through a 0.45 μm nylon filter, and the clear solution was diluted in the same solvent and its concentration was measure spectrophotometrically, based upon an extinction coefficient of 17000 at 258 nm.

EXAMPLE 2

Determination Of Biological Activity For Both Unmodified Camptothecin And Camptothecin Analogs A) Cell Culture Preparation Murine B16 melanoma cell line was grown in RPMI 1640 medium supplemented with 10% heat-inactivated fetal bovine serum, 2 mM L-glutamine, 50 units/mL penicillin, 50 μg/mL streptomycin, 25 μg/mL gentamicin, 0.75% sodium bicarbonate 10 mM HEPES buffer (pH 7.4), and 0.06 mg/mL AntiPPLO. Murine P388 leukemic cell line and human HT-29 colon adenocarcinoma line were maintained in RPMI 1640 medium supplemented with 10% heat-inactivated fetal bovine serum. P388/CPT (camptothecin resistant cell line) was maintained in RPMI 1640 medium supplemented with 20% heat-inactivated fetal bovine serum, 10 μM β-mercaptoethanol, 10 mM L-glutamine, 100 IU/mL streptomycin, and 50 μg/mL gentamicin. MCF-7M human breast adenocarcinoma was maintained in IMEM supplemented with 5% non heat-inactivated fetal bovine serum and 1 nM insulin.

B) Determination Of In Vitro Growth Inhibitory Activity

The biological assay used to test the in vitro effectiveness of the camptothecin analogs of the present invention was first described by Mosmann in 1983. [See "Rapid Colorimetric Assay For Cellular Growth And Survival: Application To Proliferation And Cytotoxicity Assays," J. Immun. Meth. 65:55 (1983)]. The assay utilizes a tetrazolium salt to quantitatively measure mammalian cell survival and proliferation by colorimetric methods. In particular, MTT, a pale yellow compound with minimal absorbance, is incubated with cancerous cells in addition to (or in the absence of) a particular camptothecin analog. Living cells with active mitochondrial enzymes metabolize the MTT into a dark blue/purple formazan product with high absorbance. The exact procedure used to test the camptothecin analogs of the present invention is described below.

Exponentially growing cells ($1-2\times10^3$ cells, unless specified otherwise) in 0.1 mL medium were seeded on day 0 in a 96-well microtiter plate. On day 1, 0.1 mL aliquots of medium containing graded concentrations of test analogs were added to the cell plates. After incubation at 37° C. in a humidified incubator for 3 days (P388, P388/CPT, B16) or 6 days (HT-29, MCF-7M), the plates were centrifuged briefly and 100 μL of the growth medium was removed. Cell cultures were incubated with 50 μL of 3-(4,5-dimethylthiazol-2-yl)-2,5-diphenyl-tetrazolium bromide [MTT, 1 mg/mL in Dulbecco's phosphate buffered saline (PBS)] for 4 hr at 37° C. The resulting purple formazan precipitate was solubilized with 200 μL of 0.04 N HCl in isopropyl alcohol. Absorbance was monitored in a BioRad Model 3550 Microplate Reader at a test wavelength of 570 nm and a reference wavelength of 630 nm. The absorbance is transferred to a PC 486 computer. The $IC_{50}$ values were determined by a computer program (EZ-ED50) that fits all of the data to the following four-parameter logistic equation:

$$Y=(A_{max}-A_{min})/(1+[X/IC^{50}])^n+A_{min}$$

where $A_{max}$ is the absorbance of control cells, $A_{min}$ is the absorbance of cells in the presence of highest agent concentration, $IC^{50}$ is the concentration of agent that inhibits the cell growth by 50% of control cells (based on the absorbance) and n is the slope of the curve.

For the in vitro cell inhibition assays, camptothecin was found to have the following $IC_{50}$ (50% cell growth inhibition concentration) as shown in Table 4:

TABLE 4

| Cell Line | $IC_{50}$ (μg/mL) |
|---|---|
| HT-29 | 0.002 |
| MCF-7 | 0.001 |
| B16 | 0.015 |
| P388 | 0.010 |
| P388/cpt | 1.123 |

The camptothecin analogs of the present invention display strong in vitro anti-cancer effectiveness. As shown in Table 5, the analogs of the present invention show in vitro activity against several of the cancerous cell lines described above.

TABLE 5

| | Growth Inhibitory Activity $IC_{50}$ (μg/mL) | | | | |
|---|---|---|---|---|---|
| Analog | P388 | P388/cpt | B16 | HT29 | MCF-7 |
| HAR4 | 0.03 | 7.04 | 0.026 | 0.011 | 0.0027 |
| HAR5 | 0.362 | 21.2 | 0.43 | 0.105 | 0.01 |
| HAR6 | 1.68 | 28.4 | 2.43 | 0.476 | 0.111 |
| HAR7 | 0.088 | 18.7 | 0.173 | 0.031 | 0.0064 |

C) Inhibition Of Topoisomerase I Catalytic Activity

The topoisomerase I catalytic activity was measured by converting the supercoiled SV40 DNA (Form I) to the relaxed form (Form $I_o$). All reactions were performed in 20 μL reaction buffer (Tris-HCl, 10 mM, pH 7.5; EDTA, 1 mM; NaCl, 100 mM) with 0.25 μg SV40 DNA, 0.5 unit of human placental topoisomerase I (TopoGen) and graded concentrations of the analog tested. The reaction mixtures were incubated at 37° C. for 30 minutes. The topoisomerase I activity was stopped by incubating the reaction mixture with 1 μL of 10% SDS and 1 μL of proteinase K (1.25 mg/mL) for additional 30 min. One μL of the loading buffer (1% bromophenol blue and 48% sucrose) was then added. Ten μL of the reaction mixture was loaded onto a 1% agarose gel prepared in TAE buffer containing 2 μg/mL chloroquine; and the electrophoresis was performed at 82 volt for 4.5 hr in the TAE buffer containing 2 μg/mL chloroquine. Chloroquine is added to separate nicked and relaxed DNA molecules; without chloroquine, the fully relaxed Form $I_o$ comigrated with the nicked DNA. The gels were then stained with 0.5 μg/mL ethidium bromide solution for 30 min or longer (if chloroquine is present during the electrophoresis step), and destained with 5 changes of deionized water. DNA bands were visualized with a 254 nm ultraviolet light (Spectroline Transilluminator Model TL-254A) and documented with a Polaroid 665 positive/negative instant pack film. The DNA bands (image) on the negative were densitometrically scanned with a Molecular Dynamic Personal Densitometer. The percent inhibition of Toposiomerase I activity is calculated based on the following equation:

% Inhibition=$(F_{SC(E+D)}-F_{SC(E)})/(F_{SC(C)}-F_{SC(E)})\times100$ where $F_{SC(E+D)}$ represents fraction of supercoiled DNA in the presence of enzyme and drug; $F_{SC(E)}$ represents fraction of supercoiled DNA in the presence of enzyme alone; $F_{SC(C)}$ represents fraction of supercoiled DNA in the untreated SV40 DNA; the $IC_{50}$ value was estimated using the same four-parameter logistic equation described in the in vitro growth inhibition studies.

The growth inhibitory activity of camptothecin (HAR1) and 6 analogs of the present invention against the P388, P388/CPT (camptothecin resistant cell line), B16, H-29, and MCF-7M tumor cells was determined using a MTT assay.

Figure 18:
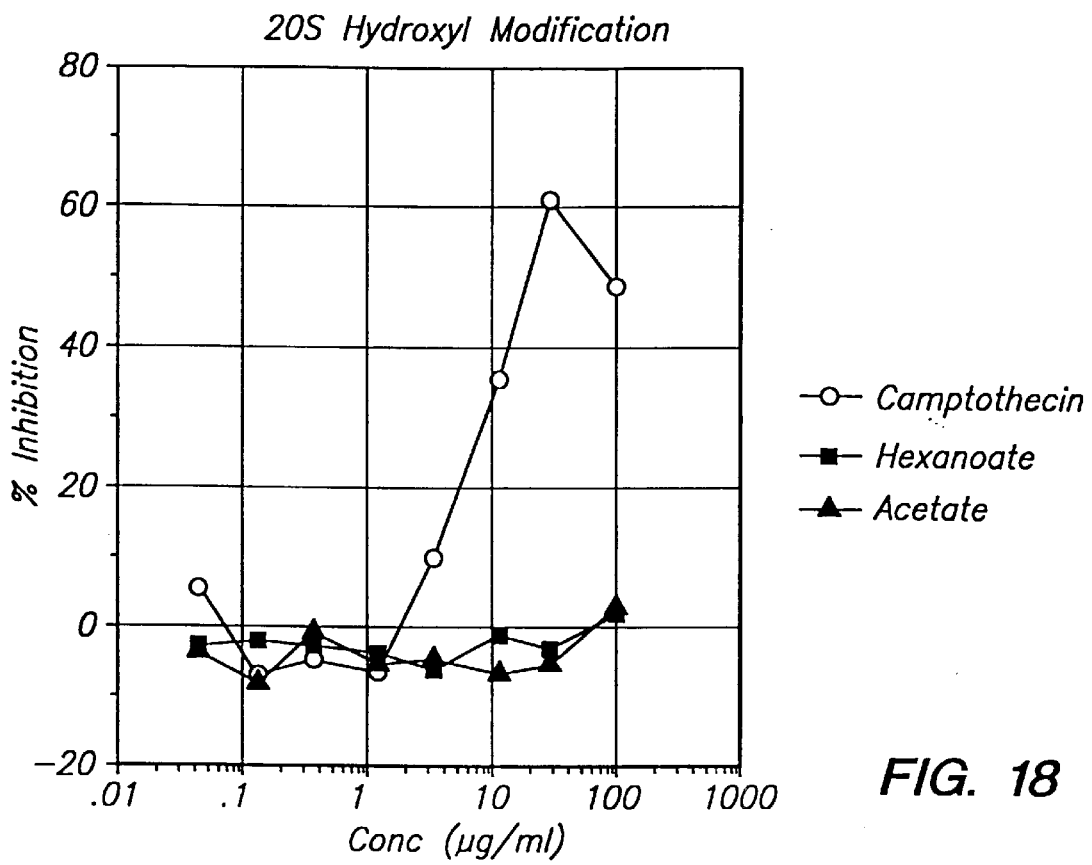
FIG. 18 shows the lack of inhibition of relaxation of supercoiled DNA by camptothecin analogs of the present invention which possessed chemical modification at the 20 position.
Figure 19:
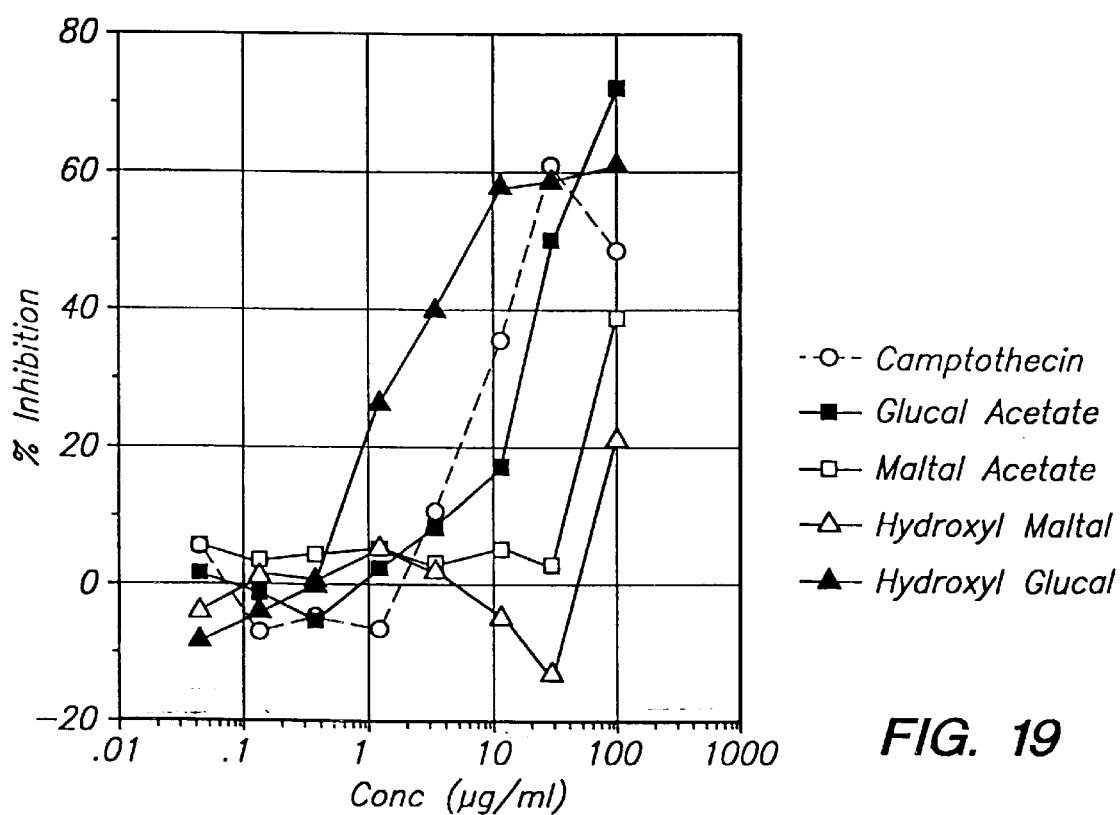
FIG. 19 shows the inhibition of relaxation of supercoiled DNA by the preferred camptothecin analogs of the present invention (HAR4, HAR5, HAR6, and HAR7).

The inhibition of topoisomerase I catalyzed relaxation of supercoiled SV40 DNA was determined by separation of supercoiled DNA by camptothecin and the six analogs of the present invention is shown in FIGS. 18 and 19. The growth inhibitory activity [expressed as $IC_{50}$ values (concentration of agents inhibits the growth of the cells by 50% of the control cells)], and the inhibitory activity of topoisomerase I [also expressed as $IC_{50}$ values (concentrations of agents which inhibits the topoisomerase I activity by 50% of the control)] of these camptothecin analogs are summarized in Tables 5 and 6.

Two different modifications were made on the camptothecin molecule. In the first modification, the 20S hydroxy group of the lactone ring (ring E) of camptothecin was converted into acetate (HAR3) or hexanoate (HAR2). The water solubility decreased from 20 μg/mL for camptothecin (HAR1) to 6.5 and 2.9 μg/mL, for the acetate (HAR3) and the hexanoate (HAR2), respectively. The growth inhibitory activity was reduced approximately 10 and 100 fold, respectively for the acetate (HAR3) and the hexanoate (HAR2). Neither the acetate (HAR3) nor the hexanoate (HAR2) inhibited the topoisomerase I activity even at the highest concentration tested (100 μg/mL). Therefore, the 20S hydroxyl group is essential for the biological activity (i.e., inhibition of Topoisomerase I activity, and growth inhibition activity).

In the second modification, either a monosaccharide [camptothecin glucal acetate, HAR4, and camptothecin hydroxyl glucal, HAR7] or disaccharide [camptothecin maltal acetate, HAR5, and camptothecin hydroxyl maltal, HAR6] was attached to the 7-hydroxymethyl group of camptothecin. The water solubility of camptothecin hydroxyl glucal and camptothecin hydroxyl maltal improved 16- and 80-fold, respectively.

The growth inhibitory activity and topoisomerase I inhibitory activity of camptothecin glucal acetate (HAR4) and camptothecin hydroxy glucal (HAR7) are quite similar to those of camptothecin. These data suggest that biological activity is retained or even enhanced if the seven position of camptothecin is appropriately substituted. It is of interest to note that camptothecin glucal acetate (HAR4) is 2–3 fold more potent in inhibiting the growth of tumor cells than camptothecin hydroxyl glucal (HAR7). However, camptothecin hydroxyl glucal (HAR7) is 10-times more inhibitory than camptothecin glucal acetate (HAR4) in the topoisomerase I assay. The reason for this disparity is unknown. It is possible that camptothecin glucal acetate (HAR4) is taken up more rapidly into cells because of greater lipophilicity. Other assays to measure trapping of enzyme cleavable complexes by these analogs might be needed to fully characterize their effects on topoisomerase I.

The growth inhibitory activity is further reduced if maltal is a substituent on the 7-hydroxymethyl group of camptothecin. A similar trend was noted as in the glucal series; camptothecin maltal acetate (HAR5) was more cytotoxic than camptothecin hydroxyl maltal (HAR6). Both compounds moderately inhibited topoisomerase I activity at the highest concentration (100 µg/mL) tested. Thus, camptothecin hydroxyl maltal (HAR6) may be a good candidate as a prodrug of 7-hydroxymethylcamptothecin. However, it remains to be determined whether this compound is converted into an "active species" in animals or humans.

All of the six analogs are cross-resistant to camptothecin as indicated in the differential growth inhibitory activity against the parent and camptothecin resistant cell lines. These data provide further support that these agents have similar mechanism as that of camptothecin.

Camptothecin was found to have a topoisomerase I $IC_{50}$ (50% activity inhibitory concentration) of 8.0 µg/mL.

The camptothecin analogs of the present invention display strong in vitro anti-cancer effectiveness. As shown in Table 6 the analogs of the present invention show significant Topoisomerase I inhibitory activity.

TABLE 6

| Analog | Topoisomerase I $IC_{50}$ (µg/mL) |
| --- | --- |
| HAR4 | 25 |
| HAR5 | >100 |
| HAR6 | >100 |
| HAR7 | 2 |

D) In Vivo Animal Testing of Camptothecin Analogs

In vivo animal testing was performed on the camptothecin analogs of the present invention using mice and five experimental tumor models; namely the murine P388 leukemia, the murine B16 melanoma, the MX-1 human breast tumor xenograft, the human lung tumor xenograft, and the human prostate tumor xenograft. For all the models, the vehicle used to deliver the analog of interest was isotonic saline.

1) Murine B16 Melanoma Model

For the B16 melanoma model, the following procedure was used. B6D2F1 mice receive i.p. inocula of B16 murine melanoma brei prepared from B16 tumors growing s.c. in mice (day 0). On day 1, tumored mice are treated with drugs of vehicle control; the route of drug administration and schedule are selected as appropriate for the study in question. If dosing information for agents is not available, the maximum tolerated dose (MTD) is determined in initial dose finding experiments in non-tumored mice. In a typical experiment, drugs are given at their MTD and ½ MTD doses i.p. on a daily×5 schedule.

The mean survival times of all groups are calculated, and results are expressed as mean survival of treated mice/mean survival of control mice (T/C)×100%. A T/C value of 150 means that the mice in the treated group lived 50% longer than those of the control group; this is sometimes referred to as the increase in life span or ILS value.

Mice that survive for 60 days are considered long-term survivors, or cures, in the B16 model. The universally accepted cut-off for activity in this model, which has been for years by the National Cancer Institute, is T/C=125. Conventional use of B16 over the years has set the following levels of activity: T/C<125, no activity, T/C=125–150, weak activity; T/C=150–200, modest activity; T/C=200–300, high activity; T/C>300, with long term survivors; excellent, curative activity.

The results for the B16 melanoma model are shown below in Table 7:

TABLE 7

| Analog | Dose | Survivors | Tox Deaths | T/C[1] | ΔWeight (%) |
| --- | --- | --- | --- | --- | --- |
| Negative Control (Saline) | N/A[1] | 0/10 | 0/10 | 100% | +11.3% |
| Positive Control (TPT) | 4 mg/kg | 0/10 | 0/10 | 212% | −7.0% |
|  | 2 mg/kg | 1/10 | 0/10 | 201% | +1.9% |
| HAR 6 | 150 mg/kg | 0/10 | 7/10 | 185% | −27.2% |
|  | 100 mg/kg | 0/10 | 1/10 | 184% | −13.8% |
| HAR 4 | 20 mg/kg | 1/10 | 1/10 | 212% | −15.6% |
|  | 10 mg/kg | 1/10 | 0/10 | 189% | +6.6% |
| HAR 5 | 200 mg/kg | 3/10 | 0/10 | 232% | +5.9% |
|  | 100 mg/kg | 3/10 | 0/10 | 239% | +9.0% |
| HAR 7 | 40 mg/kg | 1/10 | 0/10 | 205% | −7.9% |
|  | 20 mg/kg | 0/10 | 0/10 | 191% | −0.1% |

Key: 1) N/A = Not Applicable.

The high dose (150 mg/kg) of HAR 6 was lethal to mice, causing the deaths of 7/10 animals in the group. The lower dose of 100 mg/kg, proved to be the MTD, causing approximately 14% weight loss in the mice, with one drug-related death. HAR 6 administered at 100 mg/kg i.p. on a five day schedule gave a T/C value of 184 with no cures. Topotecan at doses of a 4 mg/kg and 2 mg/kg achieved T/C values of 212 and 210 respectively; one 60-day survivor was observed with the 2 mg/kg dose.

Of the four analogs (including HAR 6), HAR 5 demonstrated the highest efficacy vs. B16; three 60-day survivors ("cures") each were obtained at doses of 200 mg/kg and 100 mg/kg respectively (daily×5 schedule). T/C values for the remaining mice of 232 and 239 were achieved at the high vs. the low dose of HAR 5. HAR 4 produced one cure and a T/C=212 at its MTD of 20 mg/kg, and also gave one cure and a T/C=189 at the lower dose of 10 mg/kg (qd×5). Treatment with HAR 7 also resulted in one 60-day survivor and a T/C value of 191 (no cures). All three compounds were well-tolerated at their MTDs, with acceptable weight loss and only one toxic death (HAR 4 high dose group).

2) Murine P388 Leukemia Model

For the P388 leukemia model, the procedure followed is exactly the same as the aforementioned B16 model. The tumor inoculum is prepared by removing ascited fluid containing P388 cells from tumored B6D2F1 mice, centrifuging the cells, and then resuspending the leukemia cells in saline. Mice receive 1×10⁶ P388 cells i.p. on day 0.

The results for the P388 leukemia model are shown below in Table 8:

TABLE 8

| Analog | Dose | Survivors | Tox Deaths | T/C[1] | ΔWeight (%) |
|---|---|---|---|---|---|
| Negative Control (Saline) | N/A[1] | 0/10 | 0/10 | 100% | +17.9% |
| Positive Control (TPT) | 4 mg/kg | 3/10 | 0/10 | 297% | −6.6% |
| HAR 4 | 20 mg/kg | 2/10 | 0/10 | 206% | −14.0% |
|  | 10 mg/kg | 2/10 | 0/10 | 201% | −0.6% |
| HAR 5 | 200 mg/kg | 0/10 | 0/10 | 161% | −2.0% |
|  | 100 mg/kg | 1/10 | 0/10 | 141% | +0.7% |
| HAR 6 | 100 mg/kg | 3/10 | 0/10 | 320% | −12.2% |
|  | 50 mg/kg | 1/10 | 0/10 | 225% | −3.5% |
| HAR 7 | 40 mg/kg | 3/10 | 0/10 | 223% | −16.0% |
|  | 20 mg/kg | 0/10 | 0/10 | 192% | −1.7% |

Key: 1) N/A = Not Applicable.

The four Harrier topoisomerase I inhibitors were evaluated via i.p. administration in the same experiment vs. the murine P388 leukemia; topotecan was again included as the positive drug control. HAR 4, 6 and 7 all demonstrated high, curative efficacy on a five day schedule vs. the P388 leukemia, even though the agents diffused considerably in their potencies. HAR 6 at its MTD of 100 mg/kg produced the best antileukemic result, causing three 30-day survivors ("cures") and an impressive T/C value of 320 for the remaining seven mice. The lower dose of 100 mg/kg was less effective, but still highly active (T/C=225, with one cure).

HAR 4 and 7 also demonstrated excellent activity vs. P388. HAR 4 at 20 and 10 mg/kg produced T/C values of 206 and 201 respectively; two cures were also achieved at each dose. HAR 7 at doses of 40 and 20 mg/kg gave T/C values of 223 and 192 respectively, with three 30-day survivors recorded at the high dose. HAR 5 was less efficacious compared to the other three compounds, although one cure was obtained at the low dose of 100 mg/kg.

HAR 4, 6 and 7 were tested at their MTDs vs. P388 leukemia, as evidenced by a 12%–16% weight loss for these agents at the high dose (no toxic deaths occurred). HAR 5 was tested at its solubility-limiting dose because only insignificant weight loss was recorded for this analog.

Topotecan at its MTD of 4 mg/kg (daily×5) demonstrated a high degree of efficacy, comparable to that produced by HAR 6. Three mice treated with topotecan were recorded as 30-day survivors, and the remaining 7 animals experienced a T/C=297.

3) MX-1 Human Breast Tumor Model

For the MX-1 human breast tumor xenograft models, the following procedure was used. Nude mice are implanted s.c. by trocar with fragments of MX-1 mammary carcinomas harvested from s.c. growing MX-1 tumors in nude mice hosts. When tumors are approximately 5 mm×5 mm in size (usually about ten days after inoculation), the animals are pair-matched into treatment and control groups. Each group contains ten tumored mice, each of which is ear-tagged and followed individually throughout the experiment. The administration of drugs or vehicle begins the day the animals are pair-matched (day 1). The doses, route of drug administration and schedule are selected as appropriate for the study in question. If the MTD dose of an agent is not known, it is determined in an initial dosing experiment in non-tumored mice. In a typical experiment, drugs are given at their MTD and ½ MTD doses i.p. on a daily×5 schedule.

The experiment is usually terminated when control tumors reach a size of 2–3 g. Mice are weighed twice weekly, and tumor measurements are taken by calipers twice weekly, starting on day 1. These tumor measurements are converted to mg tumor weight by a well known formula, and from these calculated tumor weights the termination date can be determined. Upon termination, all mice are weighed, sacrificed, and their tumors excised. Tumors are weighed, and the mean tumor weight per group is calculated. In this model, the mean treated tumor weight/mean control tumor weight×100% (T/C) is subtracted from 100% to give the tumor growth inhibition for each group.

Some drugs cause tumor shrinkage in the MX-1 model. With these agents, the final weight of a given tumor is subtracted from its own weight at the start of the treatment on day 1. This difference divided by the initial tumor weight is the % shrinkage. A mean % tumor shrinkage can be calculated from data from the mice in a group that experienced MX-1 regressions. If the tumor completely disappears in a mouse, this is considered a complete regression or complete tumor shrinkage. If desired, mice with partial or total tumor regressions can be kept alive past the termination date to see whether they live to become long term, tumor-free survivors.

The camptothecin analogs of the present invention display strong in vivo anti-cancer effectiveness as well. As shown in Table 9, the analogs of the present invention show in vivo activity against MX-1 human breast xenografts implanted in mice. Note that in the following table the abbreviation SR refers to tumor shrinkage rate, while those entries followed by a superscripted '2' are tumor growth inhibition rates, not tumor shrinkage rates.

TABLE 9

| Analog | Dose | Tox Deaths | Shrinkage | SR(%)[1] | ΔWeight (%) |
|---|---|---|---|---|---|
| Negative Control (Saline) | N/A | 0/10 | 0/10 | 0% | +8.7% |
| Positive Control (Topotecan) | 4 mg/kg | 0/10 | 6/10 | 94% | −15.4% |
|  |  |  | 1/10 | 100% |  |
| HAR 6 | 50 mg/kg | 0/10 | 8/10 | 81% | +2.5% |
|  | 100 mg/kg | 1/10 | 9/10 | 94% | −18.6% |
| HAR 4 | 10 mg/kg | 0/10 | 8/10 | 77% | −10.2% |
|  |  |  | 2/10 | 100% |  |
|  | 20 mg/kg | 9/10 | 1/10 | 99% | −31/2% |
| HAR 5 | 100 mg/kg | 0/10 | 10/10 | 48%[2] | +7.4% |
|  | 200 mg/kg | 0/10 | 3/10 | 73% | +5.3% |
|  |  |  | 7/10 | 82%[2] |  |
| HAR 7 | 20 mg/kg | 0/10 | 10/10 | 98% | −0.05% |
|  | 40 mg/kg | 4/10 | 5/10 | 98% | −25.0% |

Key:
1) SR = Tumor Shrinkage Rate.
2) Tumor growth inhibition rate, not tumor shrinkage rate.

The results demonstrate that HAR 6 has impressive antitumor activity vs. MX-1. At its MTD of 100 mg/kg (qd×5), i.p. administration of HAR 6 caused extensive tumor shrinkage in 9 mice (mean shrinkage=94%); the tenth animal died of toxicity. The lower dose of 50 mg/kg caused a mean 81% tumor shrinkage in 8 mice, and 82% tumor growth inhibition in the remaining 2 animals. Topotecan at its MTD of 4 mg/kg (i.p.; daily×5) caused a mean 94% tumor shrinkage in all 10 mice.

The approximately 19% body weight loss incurred by mice treated with 100 mg/kg HAR 6 (and one drug-related death) establishes that dose as an acceptable MTD for the agent in nude mice according to NCI standards. Topotecan (TPT) at 4 mg/kg was also given at its MTD as evidenced by the 15% weight loss observed in the treated mice (no mortality).

The remaining three compounds, HAR 4, 5 and 7, were evaluated against MX-1 in a separate experiment, including an internal topotecan control. HAR 4 and HAR 7 demonstrated almost equivalent, outstanding activity against the MX-1 breast carcinoma xenograft similar to that determined for HAR 6. The 20 mg/kg of HAR 4 was toxic, and 10 mg/kg proved to be the MTD. At the dose of 10 mg/kg (daily×5), HAR 4 caused a mean 77% tumor shrinkage in 8 mice, and the complete disappearance of tumors in 2 animals. HAR 7 at the lower dose of 20 mg/kg (40 mg/kg produced lethality) caused a mean 98% tumor shrinkage in all 10 mice. Since 20 mg/kg caused virtually no weight loss (or mobility), it is possible that the somewhat higher dose of 25 or even 30 mg/kg could be the actual MTD for HAR 7.

HAR 5 at its solubility limiting dose of 200 mg/kg (weight gained by mice at this dose) caused a mean 73% tumor shrinkage in 3 mice and a mean 82% growth inhibition in 7 animals. Topotecan at its MTD of 4 mg/kg produced one complete regression, six partial responders (mean 94% tumor shrinkage) and two mice with an average 94% tumor growth inhibition. There was one drug-related death in this topotecan group. The topotecan results in the two MX-1 experiments are therefore quite reproducible.

4) Human Lung And Human Prostate Tumor Models

For the human lung and prostate tumor xenograft models the following procedure was used. Nude mice were implanted s.c. by trocar with fragments of human lung or prostate carcinomas harvested from s.c. growing tumors in nude mice hosts. When tumors were approximately 5 mm×5 mm in size (usually ten to fourteen days after inoculation), the animals were pair-matched into treatment and control groups. Each group contained 10 tumored mice, each of which was ear-tagged and followed individually throughout the experiment. The administration of drugs or vehicle begins the day the animals are pair-matched (day 1). The doses, route of drug administration and schedule were selected as appropriate for the study in question. (See above protocol). If the MTD dose of an agent was not known, it was determined in an initial dosing experiment in non-tumored mice. HAR 7 was given at its MTD and ½ MTD doses i.p. on a daily×5 and a daily×1 schedule. Topotecan was run as a positive control at its MTD dose on a daily×5 and a daily×1 schedule. Male nude mice were used for both prostate studies.

The experiment is usually terminated when control tumors reach a size of 1–2 g. Mice are weighed twice weekly, and tumor measurements were taken by calipers twice weekly, starting on day 1. These tumor measurements are converted to mg tumor weight by a well-known formula, and from these calculated tumor weights the termination date can be determined. Upon termination, all mice are weighed, sacrificed, and their tumors excised. Tumors are weighed, and the mean tumor weight per group is calculated. In these models, the mean treated tumor weight/mean control tumor weight×100% (T/C) is subtracted from 100% to give the tumor growth inhibition (TGI) for each group.

Some drugs cause tumor shrinkage in the human tumor xenograft models. With these agents, the final weight of a given tumor is subtracted from its own weight at the start of treatment on day 1. The difference divided by the initial tumor weight is the % shrinkage. A mean % tumor shrinkage can be calculated from the data from the mice in a group that experienced tumor regressions. If the tumor completely disappears in a mouse, this is considered a complete regression or complete tumor shrinkage. If desired, mice with partial or total tumor regressions can be kept alive past the termination date to see whether they live to become term, tumor-free survivors.

The results for the human lung and human prostate xenograft models are shown below in Table 10:

TABLE 10

| Model | Compound | Dose | Deaths | TGI[1] | Shrink[2] |
|---|---|---|---|---|---|
| Lung | HAR7 | 30 mg/kg × 5 days | 0/10 | 8/10 67% | 2/10 100% |
| | TPT | 4 mg/kg × 5 days | 0/10 | 8/10 66% | 2/10 55% |
| | HAR7 | 200 mg single ds | 1/10 | 7/10 64% | 2/10 67% |
| | TPT | 8 mg single ds | 0/10 | 0/10 | 0/10 |
| Prostate | HAR7 | 30 mg/kg × 5 days | 0/10 | 10/10 77% | 0/10 |
| | TPT | 3 mg/kg × 5 days | 0/10 | 10/10 35% | 0/10 |
| | HAR7 | 200 mg single ds | 0/10 | 10/10 80% | 0/10 |
| | HAR7 | 100 mg single ds | 0/10 | 9/10 51% | 1/10 20% |
| | TPT | 8 mg single ds | 0/10 | 0/10 | 0/10 |

Key:
1) TGI = Number of Animals Experiencing Tumor Growth Inhibition; and % Tumor Growth Inhibition Rate.
2) Shrink = Number of Animals Experiencing Tumor Shrinkage; and % Tumor Shrinkage Rate.

The compound, HAR 7, was evaluated against both the lung and prostate models with an internal topotecan control. HAR7 demonstrated outstanding activity against the lung and prostate xenograft models. At the dose of 30 mg/kg (daily×5), HAR 7 caused the complete disappearance of tumors in 2 animals with lung xenografts. At the dose of 30 mg/kg (daily×5), HAR 7 caused a mean tumor growth inhibition of 77% in all ten animals having the prostate xenograft.

Even more encouraging were the single dose results for HAR7 which resulted in significant tumor growth inhibition and even some animals experiencing partial cures for both the lung and prostate xenograft models. By comparison a single dose of TPT was completely ineffective for both models. This is indeed a rare occurrence, as single doses of chemotherapeutic agents are usually ineffective.

EXAMPLE 3

Synthesis Of Novel Camptothecin Analogs

A) Synthesis Of 7-Hydroxymethylcamptothecin

Figure 3:
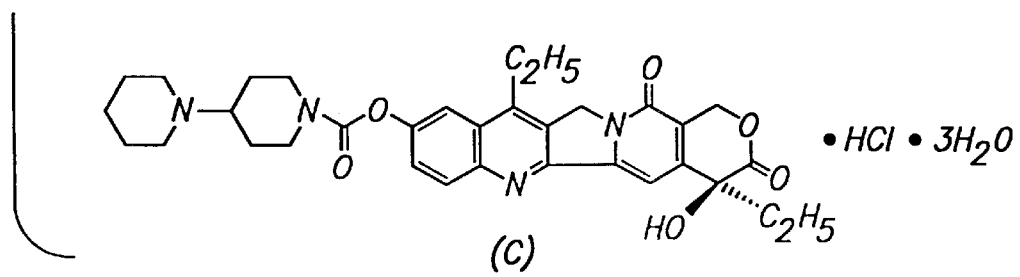
FIG. 3 shows the structure of 7-hydroxymethyl camptothecin, an intermediate in the chemical synthesis of the camptothecin analogs of the present invention.
Figure 3:
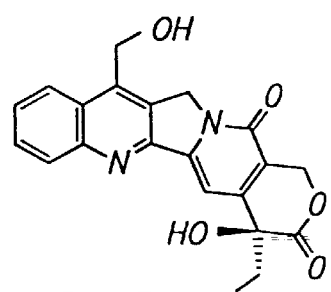
Figure 4:
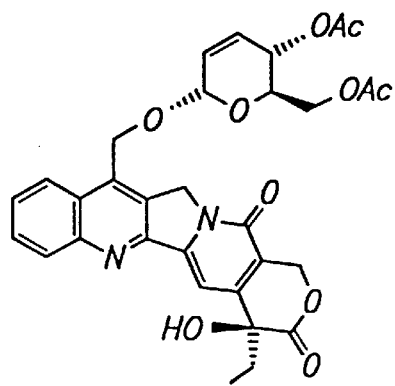
FIG. 4 shows the structure of a preferred camptothecin analog of the present invention, 7-[4,6-di-O-acetyl-2,3-dideoxy-α-D-erythro-hex-2-enopyranosyl]-oxymethylcamptothecin (HAR4).
Figure 5:
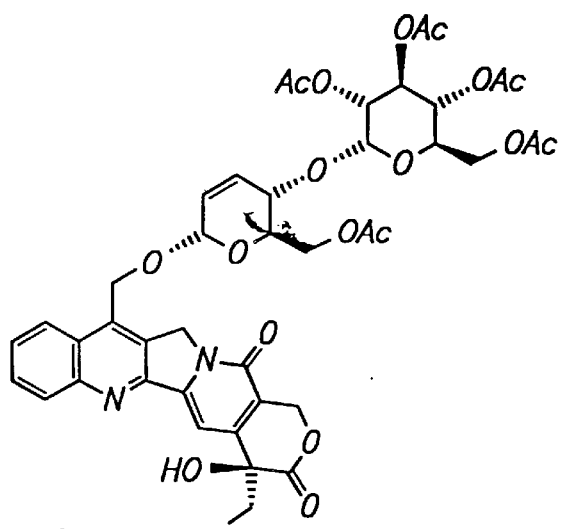
FIG. 5 shows the structure of a preferred camptothecin analog of the present invention, 7-[6-O-acetyl-4-O-(2,3,4,6-tetra-O-acetyl-α-D-glucopyranosyl)-2,3-dideoxy-α-D-erythro-hex-2-enopyranosyl]oxymethylcamptothecin (HAR5).
Figure 6:
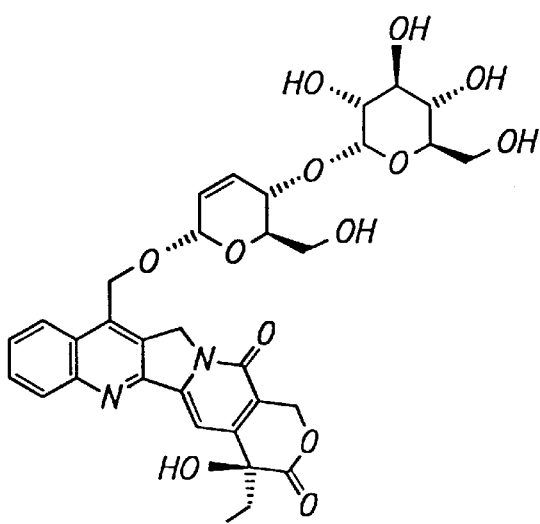
FIG. 6 shows the structure of a preferred camptothecin analog of the present invention, 7-[4-O-(α-D-glucopyranosyl)-2,3-dideoxy-α-D-erythro-hex-2-enopyranosyl]oxymethylcamptothecin (HAR6).
Figure 7:
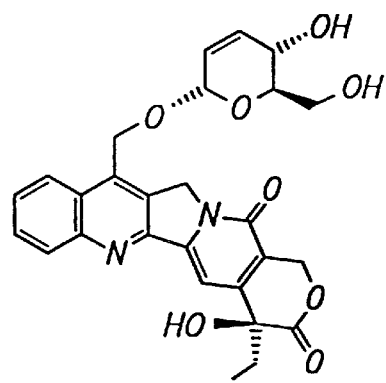
FIG. 7 shows the structure of a preferred camptothecin analog of the present invention, 7-[2,3-dideoxy-α-D-erythro-hex-2-enopyranosyl]oxymethylcamptothecin (HAR7).
Figure 8:
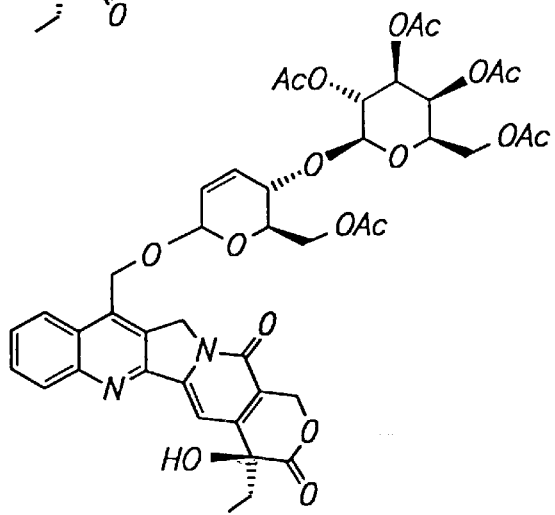
FIG. 8 shows the structure of a preferred camptothecin analog of the present invention, 7-[6-O-acetyl-4-O-(2,3,4,6-tetra-O-acetyl-β-D-galactopyranosyl)-2,3-dideoxy-α-D-erythro-hex-2-enopyranosyl]-oxymethylcamptothecin.
Figure 9:
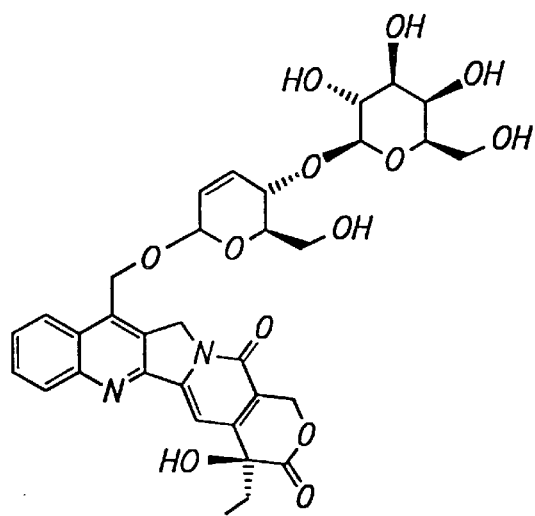
FIG. 9 shows the structure of a preferred camptothecin analog of the present invention, 7-[4-O-(β-D-galactopyranosyl)-2,3-dideoxy-α-D-erythro-hex-2-enopyranosyl]-oxymethylcamptothecin
Figure 10:
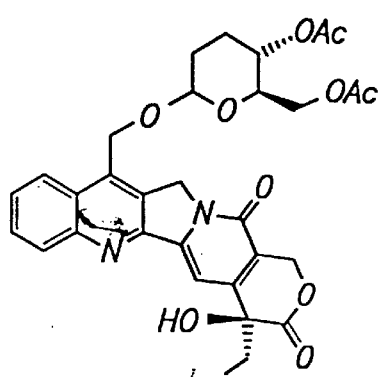
FIG. 10 shows the structure of a preferred camptothecin analog of the present invention, 7-[4,6-di-O-acetyl-2,3-dideoxy-α-D-erythro-hexanopyranosyl]-oxymethylcamptothecin.
Figure 11:
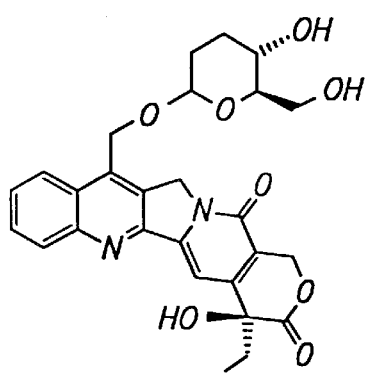
FIG. 11 shows the structure of a preferred camptothecin analog of the present invention, 7-[2,3-dideoxy-α-D-erythro-hexanopyranosyl]-oxymethylcamptothecin.
Figure 12:
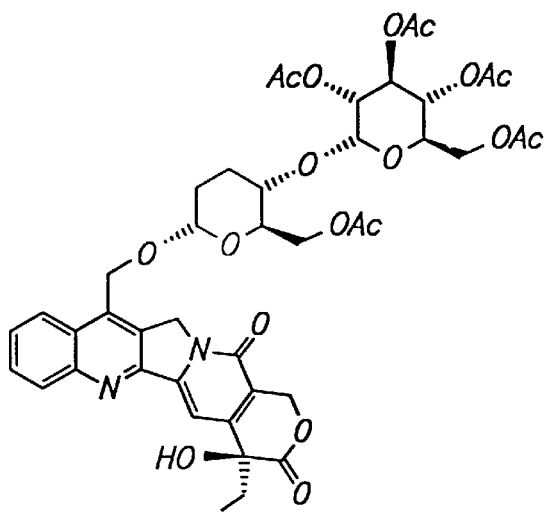
FIG. 12 shows the structure of a preferred camptothecin analog of the present invention, 7-[6-O-acetyl-4-O-(2,3,4,6-tetra-O-acetyl-α-D-glucopyranosyl)-2,3-dideoxy-α-D-erythro-hexanopyranosyl]-oxymethylcamptothecin.
Figure 13:
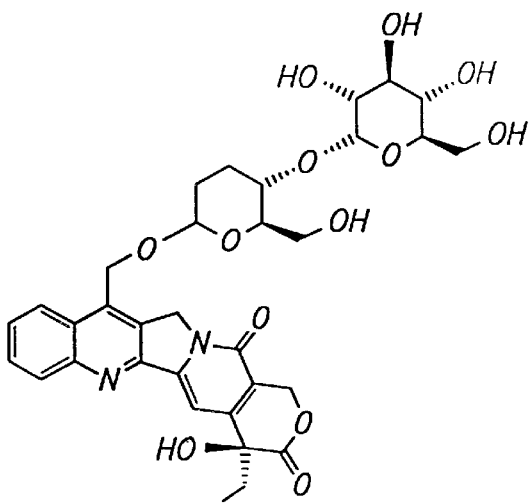
FIG. 13 shows the structure of a preferred camptothecin analog of the present invention, 7-[4-O-(α-D-glucopyranosyl)-2,3-dideoxy-α-D-erythro-hexanopyranosyl]-oxymethylcamptothecin.
Figure 14:
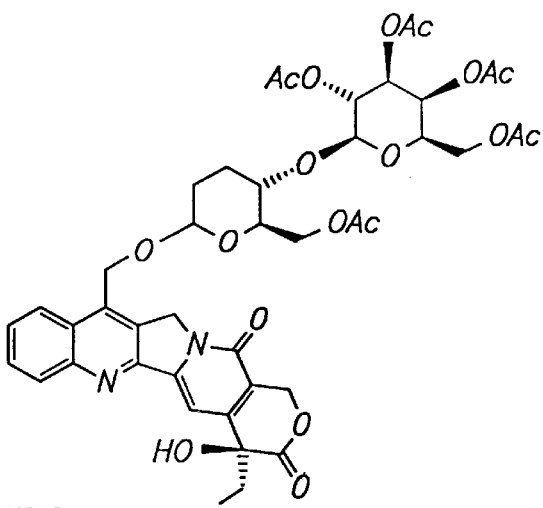
FIG. 14 shows the structure of a preferred camptothecin analog of the present invention, 7-[6-O-acetyl-4-O-(2,3,4,6-tetra-O-acetyl-β-D-galactopyranosyl)-2,3-dideoxy-α-D-erythro-hexanopyranosyl]-oxymethylcamptothecin.

The procedure used to synthesize 7-hydroxymethyl-camptothecin (FIG. 3) was a modified version of the original procedure described by Sawada. [See Sawada et al., Chem. Pharm. Bull. 39:2574 (1991)].

Camptothecin (20.0 g) was dissolved in mixture of methanol (750 mL), water (500 mL), conc. $H_2SO_4$ (500 mL) and finely ground $FeSO_4$ (16.0 g) and hydrogen peroxide (100 mL 30% solution) was added dropwise over the course of 2 h and the reaction mixture was allowed to stir for another hour. The reaction mixture was then filtered through a sintered glass funnel to remove all undissolved material. The resultant filtrate was then cooled to 0° C. and NaOH (375 g) in 1 L water was added slowly with vigorous stirring. The yellow-brown solid was then filtered, washed with water and pumped to dryness. The resultant crude product was then placed in a 1 L erlenmyer flask, DMF (300 mL) added and warmed to 110° C. Once the solid is dispersed into small particles, acetonitrile (500 mL) was added and the mixture heated until boiling. The mixture was then allowed to cool to room temperature then 0° C., filtered and the solid washed with chloroform to provide 7-hydroxymethylcamptothecin (21.50 g, 99%) as a pale yellow solid.

B) Synthesis Of Tri-O-acetyl-D-glucal

Tri-O-acetyl-D-Glucal was synthesized according to the following procedure. Alternatively it could be commercially obtained from Pfanstiehl Laboratories Inc. (Wankeyan, Ill.), however the procedure described below has the advantage of reduced cost compared to the commercial source.

Glucose (1.000 g) was suspended in a solution of acetic acid (10 mL) and acetic anhydride (3.606 g, 7.0 equiv) and 1.000 g 31% HBr/acetic acid solution added. The reaction mixture was allowed to stir for 1 h, after which 9.000 g more 31% HBr/acetic acid solution (total of 7.7 equiv HBr) was added and allowed to stir overnight. Sodium acetate was then added (2.700 g) to neutralized the excess HBr, and the reaction mixture was added to a suspension containing pulverized $CuSO_4 \cdot 5H_2O$ (0.315 g), zinc (12.600 g), water (10 mL), sodium acetate (9.450 g), and acetic acid (5 mL) and the resultant reaction mixture was stirred vigorously for 1.5 h. The solution was then filtered and the solid washed with ethyl acetate (100 mL) and water (100 mL). The organic layer of the filtrate was then washed with $NaHCO_3$ (100 mL) and brine (50 mL), dried ($Na_2SO_4$), filtered and the solvent removed under reduced pressure to provide tri-O-acetyl-D-glucal (1.350 g, 98%) as a colorless oil free of impurities as judged by $^1H$ NMR.

C) Synthesis Of Di-O-acetyl-(o-methoxy)benzoyl Glucal

Tri-O-acetyl-D-glucal (1.000 g) was dissolved with o-anisic acid (0.671 g, 1.2 equiv.) and iodine (0.186 g, 0.2 equiv.) in 45 mL THF and quickly cooled to −78° C. A 1 mm Hg vacuum line was then attached and the reaction mixture allowed to warm slowly to −5° C. This reaction mixture was allowed to stir for 2 h under these conditions, replacing the lost THF solvent periodically. The reaction mixture was then poured into 50 mL ethyl acetate and washed successively with saturated $Na_2S_2O_3$, saturated $NaHCO_3$, and brine. The organic layer was then dried over $Na_2SO_4$, filtered and the solvent removed under reduced pressure. The resultant crude oil was purified by silica gel chromatography (75% ethyl acetate in hexane) to provide diacetyl-(o-methoxy) benzoyl glucal (1.141 g, 85%) as a mixture of 4 isomers. A 6:1 mixture of the α and β isomers could be separated from a 1.4:1 mixture of 3R and 3S isomers for spectral analysis by silica gel chromatography (20% ethyl acetate). While isomers are produced using this procedure, under the conditions in which the isomeric mixture is subsequently added to the 7-hydroxymethylcamptothecin (see below), a single intermediate is formed resulting in a single final stereochemical product.

α anomer: TLC $R_f$ 0.56 (2:1 ethyl acetate:hexanes); $[\alpha]_D^{20}$+18.9° (c=1.02, $CHCl_3$) $^1H$ NMR (360 MHz, $CDCl_3$) δ2.066 (s, 3H), 2.117 (s, 3H), 3.910 (s, 3H), 4.260 (m, 3H), 5.431 (ddd, J=9.5, 3.2, 1.6 Hz, 1H), 5.999 (1H) and 6.060 (1H) (ABq, $J_{AB}$=10.2 Hz, the 5.999 peaks are further split into dd with J=2.8, 1.9 Hz, the 6.060 peaks are further split into dd with J=0.8, 0.8 Hz), 6.563 (ddd, J=2.8, 0.9, 0.9 Hz, 1H), 6.994 (m, 2H), 7.505 (ddd, J=8.1, 7.5, 1.8 Hz, 1H), 7.816 (dd, J=8.1, 1.8 Hz, 1H); $^{13}C$ NMR (90 MHz, $CDCl_3$) δ20.69 (q), 20.91 (q), 55.94 (q), 62.57 (t), 64.80 (d), 69.17 (d), 88.33 (d), 112.11 (d), 119.31 (s), 120.09 (d), 126.18 (d), 130.53 (d), 131.74 (d), 159.51 (s), 164.56 (s), 170.08 (s), 170.77 (s); IR (KBr) 759 (w), 926 (m), 1044 (m), 1193 (w), 1236 (s), 1294 (w), 1371 (w), 1438 (w), 1466 (w), 1492 (w), 1601 (w), 1743 (s) $cm^{-1}$.

3R and 3S isomers: TLC $R_f$ 0.62 (2:1 ethyl acetate:hexanes); $[\alpha]_D^{20}$+30.4° (c=1.01, $CHCl_3$); $^1H$ NMR (300 MHz, $CDCl_3$) δ2.034 (s, 3H, 3S isomer), 2.0931 (s, 3H, 3R isomer), 2.096 (s, 3H, 3R isomer), 2.099 (s, 3H, 3S isomer), 3.900 (s, 3H), 4.218–4.534 (m, 3H), 5.037 (m, 1H), 5.236 (dd, J=10.1, 3.7 Hz, 1H, 3R isomer), 5.390 (dd, J=6.8, 5.8 Hz, 1H, 3S isomer), 5.544 (dd, J=4.6, 3.8 Hz, 1H, 3S isomer), 5.709 (dd, J=6.8, 3.8 Hz, 1H, 3R isomer), 6.505 (d, J=6.2 Hz, 1H, 3S isomer), 6.580 (d, J=5.9 Hz, 1H, 3R isomer), 7.004 (m, 2H), 7.485 (m, 1H), 7.784 (m, 1H); $^{13}C$ NMR (90 MHz, $CDCl_3$) δ20.74 (q, 2C), 55.95 (q), 61.64 (t, 3S isomer), 62.04 (t, 3R isomer), 66.67 (d), 67.26 (d, 3R isomer), 67.34 (d, 3S isomer), 70.78 (d, 3R isomer), 74.04 (d, 3S isomer), 97.77 (d, 3R isomer), 99.16 (d, 3S isomer), 111.98 (d, 3S isomer), 112.15 (d, 3R isomer), 119.90 (s), 120.16 (d), 131.47 (d, 3R isomer), 131.99 (d, 3S isomer), 133.73 (d, 3R isomer), 134.05 (d, 3S isomer), 145.56 (d, 3S isomer), 147.92 (d, 3R isomer), 159.30 (s), 165.36 (s), 169.54 (s), 170.69 (s); IR (KBr) 758 (w), 1076 (m), 1128 (s), 1227 (w), 1295 (w), 1369 (w), 1438, 1468 (w), 1492 (w), 1601 (w), 1647 (w), 1744 (s) $cm^{-1}$.

D) Synthesis Of 7-[4,6-Di-O-acetyl-2,3 dideoxy-α-D-erythro-hex-2-enopyranosyl]oxymethylcamptothecin (HAR4)

Toluene sulfonic acid monohydrate (4.500 g) was placed in a 100 mL rounded bottomed flask and heated at reduced pressure until all of the solid was melted and the water removed. THF (30 mL), 7-hydroxymethyl camptothecin (1.500 g) and iodine (0.500 g) was added and diacetyl-(o-methoxy)benzoyl glucal (5.000 g) in THF (30 mL) was added dropwise over the course of 2 h and the resultant reaction mixture was allowed to stir overnight. The reaction mixture was then poured into ethyl acetate (200 mL) and the organic layer was washed with saturated $Na_2S_2O_3$ (100 mL), saturated $NaHCO_3$ (100 mL), and brine (50 mL). The organic layer was then dried over $Na_2SO_4$, filtered, and concentrated and the resultant crude solid purified by silica gel chromatography (gradient of 50% ethyl acetate in hexanes to 100% ethyl acetate) to give 7-[4,6-di-O-acetyl-2,3 dideoxy-α-D-erythro-hex-2-enopyranosyl]-hydroxymethylcamptothecin (2.021 g, 86%) as a yellow solid.

mp 99–101° C.; $[\alpha]_D^{20}$+49.0° (c=1.00, $CHCl_3$); $^1H$ NMR (300 MHz, $CDCl_3$) δ1.042 (dd, J=7.3, 7.3 Hz, 3H), 1.905 (dq, J=7.3, 7.3 Hz, 2H), 2.098 (s, 6 H), 3.870 (s, 1H, OH), 4.091–4.279 (m, 3H), 5.187–5.576 (m, 7H), 5.739 (d,J=16.4 Hz, 1H), 5.942 (1H) and 6.010 (1H) (ABq, $J_{AB}$=10.3 Hz, the 5.942 peaks are further split into dd with J=2.0, 2.0 Hz), 7.666 (s, 1H), 7.678 (m, 2H), 7.824 (ddd, J=8.3, 6.8, 1.3 Hz, 1H), 8.066 (d, J=7.7 Hz, 1H), 8.245 (d, J=8.3 Hz, 1H); $^{13}C$ NMR (90 MHz, $CDCl_3$) δ7.63 (q), 20.61 (q), 20.76 (q), 31.45 (t), 50.24 (t), 62.63 (t), 64.89 (t), 65.08 (t), 66.11 (d), 67.43 (d), 72.56 (s), 94.37 (d), 97.72 (d), 118.54 (s), 123.02 (d), 125.62 (d), 126.38 (d), 127.04 (s), 127.97 (d), 130.08 (d), 130.24 (d), 130.41 (d), 138.13 (s) 146.02 (s), 148.71 (s), 149.86 (s), 152.34 (s), 157.34 (s), 170.04 (s), 170.48 (s), 173.61 (s); IR (KBr) 1051 (m), 1156 (w), 1231 (s), 1371 (m), 1448 (w), 1512 (w), 1610 (m), 1661 (m), 1745 (s), 3459 (w) $cm^{-1}$.

E) Synthesis Of 7-[2,3-Dideoxy-α-D-erythro-hex-2-enopyranosyl camptothecin (HAR7)

7-[4,6-di-O-acetyl-2,3 dideoxy-α-D-erythro-hex-2-enopyranosyl]-hydroxymethyl-camptothecin (1.000 g) was placed in a 50 mL rounded bottom flask and 25 mL methanol was added. The mixture was then cooled to 0° C. and $NH_3$ was bubbled through (8.100 g dissolved) and the reaction mixture was allowed to stir overnight. The solvent was then removed under reduced pressure and the resultant crude purified by silica gel chromatography (5% methanol in ethyl acetate) to provide 7-[2,3-dideoxy-α-D-erythro-hex-2- enopyranosyl]-hydroxymethylcamptothecin (0.630 g, 73%) as a light yellow solid.

mp 188° C. (dec.); [α]$_D^{20}$+13.7° (c=0.40, DMSO); $^1$H NMR (360 MHz, DMSO) δ0.890 (dd, J=7.4, 7.4 Hz, 3H), 1.879 (m, 2 H), 3.434–3.560 (m, 3H), 3.874 (m, 1H), 4.692 (dd, J=5.7, 5.7 Hz, 1H, OH), 5.147 (d, J=6.6 Hz, 1H), 5.255 (m, 2H), 5.384 (s, 2H), 5.395 (m, 1H), 5.436 (s, 2H), 5.745 (1H) and 5.910 (1H) (ABq, J$_{AB}$=10.0 Hz, the 5.745 peaks are further split into dd with J=2.3, 2.3 HZ), 6.542 (s, 1H, OH), 7.349 (s, 1H), 7.746 (dd, J=7.1, 7.0 Hz, 1H), 7.880 (ddd, J=8.4, 7.0, 1.3 Hz, 1H), 8.194 (dd, J=7.1, 1.3 Hz, 1H), 8.311 (d, J=8.4 Hz, 1H); $^{13}$C NMR (90 MHz, DMSO) δ172.39 (s), 156.68 (s), 152.36 (s), 149.90 (s), 148.12 (s), 145.40 (s), 138.94 (s), 135.22 (d), 130.03 (d), 129.56 (d), 128.31 (s), 127.66 (d), 126.02 (s), 124.69 (d), 124.45 (d), 118.99 (s), 96.56 (d), 93.72 (d), 73.36 (d), 72.30 (s), 65.18 (t), 63.88 (t), 62.24 (d), 60.65 (t), 50.12 (t), 30.21 (t), 7.71 (q); IR (KBr) 1026 (s), 1055 (s), 1159 (m), 1231 (w), 1384 (m), 1512 (w), 1597 (s), 1658 (s), 1746 (s), 3402 (m) cm$^{-1}$.

F) Synthesis Of Hexa-O-acetyl maltal

The procedure used to synthesize hexa-O-acetyl maltal (not commercially available) is described below. This procedure has the advantage of using the same solvent for the entire workup. Maltose monohydrate (1.000 g 90% maltose, 10% glucose and maltatriose) was suspended in a solution of acetic acid (10 mL) and acetic anhydride (2.833 g, 10.0 equiv) and 1.000 g 31% HBr/acetic acid solution added. The reaction mixture was allowed to stir for 1 h, after which 9.000 g more 31% HBr/acetic acid solution was added and allowed to stir overnight. The reaction mixture was then poured into a suspension containing pulverized CuSO$_4$·5H$_2$O (0.182 g), zinc (7.290 g), water (10 mL), sodium acetate (5.470 g), and acetic acid (5 mL) and the resultant reaction mixture was stirred vigorously for 1.5 h. The solution was then filtered and the solid washed with ethyl acetate (100 mL) and water (100 mL). The organic layer of the filtrate was then washed with NaHCO$_3$ (100 mL) and brine (50 mL), dried (Na$_2$SO$_4$), filtered and the solvent removed under reduced pressure to provide a colorless oil which was purified by silica gel chromatography (50% ethyl acetate/hexanes) to give hexa-O-acetyl-maltal (1.210 g, 86%) as a colorless solid and tri-O-acetyl-D-glucal (0.132 g, 88%) as a colorless oil. Regarding the maltose starting material, a more pure commercial sample would be preferred, obviating the need for the aforementioned chromatographic separation.

G) Synthesis Of Penta-O-Acetyl-O-(o-methoxy) benzoylmaltal

Hexa-O-acetylmaltal (1.000 g) was dissolved with o-anisic acid (0.326 g, 1.2 equiv.) and iodine (0.090 g, 0.2 equiv.) in 45 mL THF and quickly cooled to −78° C. A 1 mm Hg vacuum line was then attached and the reaction mixture allowed to warm slowly to −5° C. This reaction mixture was allowed to stir for 3 h under these conditions, replacing the lost THF solvent periodically. The reaction mixture was then poured into 50 mL ethyl acetate and washed successively with saturated Na$_2$S$_2$O$_3$, saturated NaHCO$_3$, and brine. The organic layer was then dried over Na$_2$SO$_4$, filtered and the solvent removed under reduced pressure. The resultant crude oil was purified by silica gel chromatography (75% ethyl acetate in hexane) to provide pentaacetyl-(o-methoxy) benzoyl maltal (1.103 g, 95%) as a mixture of 4 isomers. An 8:1 mixture of the α and β isomers could be separated from a mixture of 3R and 3S isomers along with a small amount of starting hexa-O-acetylmaltal for spectral analysis by silica gel chromatography (20% ethyl acetate).

α anomer: mp 59–60° C.; TLC R$_f$ 0.48 (2:1 ethyl acetate:hexanes); [α]$_D^{20}$+118.4° (c=1.03, CHCl$_3$); $^1$H NMR (360 MHz, CDCl$_3$) δ2.013 (s, 3H), 2.031 (s, 3H), 2.040 (s, 3H), 2.089 (s, 3H), 2.105 (s, 3H), 3.373–4.517 (m, 7H), 3.928 (s, 3H), 4.717–5.512 (m, 4H), 5.991 (1H) and 6.012 (1H) (ABq, J$_{AB}$=10.3), 6.526 (br s), 7.014 (m, 2H), 7.521 (dd, J=8.2, 7.5 Hz, 1H), 7.844 (d, J=7.6 Hz, 1H); $^{13}$C NMR (90 MHz, CDCl$_3$) δ20.54 (q, 5C), 55.98 (q), 61.73 (t), 63.05 (t), 68.35 (d, 3C), 69.78 (d, 3C), 70.74 (d), 88.21 (d), 94.44 (d), 112.19 (d), 119.53 (s), 120.10 (d), 126.24 (d), 129.84 (d), 131.65 (d), 133.83 (d), 159.39 (s), 164.46 (s), 169.19 (s), 169.71 (s), 169.82 (s), 170.16 (s, 2C); IR (KBr) cm$^{-1}$.

H) Synthesis Of 7-[6-O-Acetyl-4-O-(2,3,4,6-tetra-O-acetyl-α-D-glucopyranosyl)-2,3-dideoxy-α-D-erythro-hex-2-enopyranosyl]oxymethylcamptothecin (HAR5)

Toluene sulfonic acid monohydrate (0.590 g) was placed in a 25 mL rounded bottomed flask and heated at reduced pressure until all of the solid was melted and the water removed. THF (10 mL), 7-hydroxymethyl camptothecin (0.200 g) and iodine (0.100 g) was added and pentaacetyl-benzoyl maltal (1.000 g) in THF (10 mL) was added dropwise over the course of 1 h and the resultant reaction mixture was allowed to stir overnight. The reaction mixture was then poured into ethyl acetate (100 mL) and the organic layer was washed with saturated Na$_2$S$_2$O$_3$ (50 mL), saturated NaHCO$_3$ (50 mL), and brine (25 mL). The organic layer was then dried over Na$_2$SO$_4$, filtered, and concentrated and the resultant crude solid purified by silica gel chromatography (gradient of 50% ethyl acetate in hexanes to 100% ethyl acetate) to give 7-[6-O-acetyl-4-O-(2,3,4,6-tetra-O-acetyl-α-D-glucopyranosyl)-2,3-dideoxy-α-D-erythro-hex-2-enopyranosyl]-hydroxymethylcamptothecin (0.280 g, 61%) as a pale yellow solid.

mp 139–142° C.; [α]$_D^{20}$+103.1° (c=1.00, CHCl$_3$); $^1$H NMR (300 MHz, CDCl$_3$) δ1.026 (dd, J=7.4, 7.4 Hz, 3H), 1.909 (m, 2H), 2.003 (s, 3H), 2.025 (s, 3H), 2.060 (s, 3H), 2.102 (s, 3H), 2.155 (s, 3H), 4.020–4.4.357 (m, 7H) 4.839 (dd, J=3.9, 10.3 Hz, 1H), 5.065 (dd, J=9.7, 9.8 Hz, 1H), 5.165–5.494 (m, 7H), 5.709 (d, J=6.3 Hz, 1H), 5.941 (br s, 2H), 7.670 (s, 1H), 7.678 (dd, J=7.5, 7.5 Hz, 1H), 7.817 (dd, J=7.5, 7.5 Hz), 8.103 (d, J=7.5 Hz), 8.245 (d, J=7.5 Hz, 1H); $^{13}$C NMR (90 MHz, CDCl$_3$) δ7.83 (q), 20.60 (q), 20.64 (q), 20.69 (q, 2C), 20.87 (q), 31.65 (t), 50.17 (t), 63.10 (t), 64.77 (t), 66.28 (t), 67.99 (t), 68.14 (d), 68.25 (d), 69.52 (d), 69.72 (d), 70.67 (d), 72.79 (s), 94.10 (d), 94.32 (d), 97.97 (d), 118.80 (s), 123.45 (d), 126.13 (d), 126.78 (d), 127.68 (s), 128.24 (d), 129.62 (d), 130.31 (d), 130.57 (d), 138.05 (s), 146.25 (s), 149.05 (s), 150.03 (s), 152.47 (s), 157.49 (s), 169.54 (s), 169.98 (s), 170.34 (s), 170.54 (s), 170.58 (s, 2C), 173.77 (s); IR (KBr) 1038 (s), 1137 (w), 1229 (s), 1369 (m), 1436 (w), 1614 (m), 1662 (m), 1748 (s), 3471 (w) cm$^{-1}$.

I) Synthesis Of 7-[4-O-(α-D-Glucopyranosyl)-2,3-dideoxy-α-D-erythro-hex-2-enopyranosyl]-oxymethylcamptothecin (HAR6)

7-[6-O-acetyl-4-O-(2,3,4,6-tetra-O-acetyl-α-D-glucopyranosyl)-2,3-dideoxy-α-D-erythro-hex-2-enopyranosyl]-hydroxymethylcamptothecin (2.600 g) was placed in a 50 mL rounded bottom flask and 25 mL methanol was added. The mixture was then cooled to 0° C. and NH$_3$ was bubbled through (5.000 g dissolved) and the reaction mixture was allowed to stir overnight. The solvent was then removed under reduced pressure and the resultant crude purified by silica gel chromatography (5% methanol in ethyl acetate) to provide 7-[4-O-(α-D-glucopyranosyl)-2,3-dideoxy-α-D-erythro-hex-2-enopyranosyl]-hydroxymethylcamptothecin (1.580 g, 80%) as a light yellow solid.

mp 197–199° C.; $[\alpha]_D^{20}$+75.4° (c=1.00, DMF); $^1$H NMR (300 MHz, DMSO) δ0.887 (dd, J=7.3, 7.3 Hz, 3H), 1.873 (m, 2 H), 3.037–3.675 (m, ), 4.107 (d, J=10.2 Hz, 1H), 4.477 (m, 1 H, OH), 4.741 (m, 3H, OH), 4.858 (br s, 1H, OH), 4.889 (d, J=4 Hz, 1H), 5.270 and 5.394 (ABq, $J_{AB}$=12.8 Hz; the 5.394 pm peaks also form an AB pattern with the peaks at 5.440 pm) and 5.440 (ABq, $J_{AB}$=12.4 Hz), 5.832 (br d, J=10.0 Hz, 1H), 6.160 (d, J=10.0 Hz, 1H), 6.517 (s, 1H, OH), 7.350 (s, 1H), 7.750 (dd, J=7.4, 7.6 Hz, 1H), 7.879 (dd, J=7.4, 7.6 Hz, 1H), 8.184 (d, J=7.4 Hz, 1H), 8.315 (d, J=7.4 Hz, 1H); $^{13}$C NMR (75 MHz, DMSO) δ7.71 (q), 30.24 (t), 50.08 (t), 60.72 (t, 2C), 64.01 (t), 65.18 (t), 67.16 (d), 70.00 (d), 70.98 (d), 71.43 (d), 72.30 (s), 72.93 (d), 73.39 (d), 93.80 (d), 96.24 (d), 96.58 (d), 118.99 (s), 124.41 (d), 125.82 (d), 125.97 (s), 127.68 (d), 128.29 (s), 129.53 (d), 130.03 (d), 130.77 (d), 138.76 (s), 145.36 (s), 148.09 (s), 149.88 (s), 152.31 (s), 156.66 (s), 172.39 (s); IR (KBr) 1024 (s), 1051 (s), 1152 (m), 1231 (w), 1255 (w), 1280 (w), 1401 (w), 1511 (w), 1597 (s), 1658 (s), 1745 (s), 3394 (m) cm$^{-1}$.

J) Synthesis Of Hexa-O-acetyl-lactal

Lactose (1.000 g) was suspended in a solution of acetic acid (10 mL) and acetic anhydride (2.680 g, 9.0 equiv) and 1.000 g 31% HBr/acetic acid solution added. Although the solid lactose was not dissolved after the reaction mixture was allowed to stir for 1 h, 9.000 g more 31% HBr/acetic acid solution was added and allowed to stir overnight. The reaction mixture was then poured into a suspension containing pulverized $CuSO_4 \cdot 5H_2O$ (0.182 g), zinc (7.290 g), water (10 mL), sodium acetate (5.470 g), and acetic acid (5 mL) and the resultant reaction mixture was stirred vigorously for 1.5 h. The solution was then filtered and the solid washed with ethyl acetate (100 mL) and water (100 mL). The organic layer of the filtrate was then washed with $NaHCO_3$ (100 mL) and brine (50 mL), dried ($Na_2SO_4$), filtered and the solvent removed under reduced pressure to provide a colorless solid which was purified by silica gel chromatography (50% ethyl acetate/hexanes) to give hexa-O-acetyl-lactal (1.010 g, 61%).

K) Synthesis Of Penta-O-Acetyl-O-(o-methoxy) benzoyllactal

Hexa-O-acetyllactal (1.000 g) was dissolved with o-anisic acid (0.326 g, 1.2 equiv.) and iodine (0.090 g, 0.2 equiv.) in 45 mL THF and quickly cooled to −78° C. A 1 mm Hg vacuum line was then attached and the reaction mixture allowed to warm slowly to −5° C. This reaction mixture was allowed to stir for 3 h under these conditions, replacing the lost THF solvent periodically. The reaction mixture was then poured into 50 mL ethyl acetate and washed successively with saturated $Na_2S_2O_3$, saturated $NaHCO_3$, and brine. The organic layer was then dried over $Na_2SO_4$, filtered and the solvent removed under reduced pressure. The resultant crude oil was purified by silica gel chromatography (75% ethyl acetate in hexane) to provide penta-O-acetyl-O-(o-methoxy)benzoyl lactal (1.003 g, 86%) as a inseparable mixture of 4 isomers.

L) Synthesis Of 7-[6-O-acetyl-4-O-(2,3,4,6-tetra-O-acetyl-β-D-galactopyranosyl)-2,3-dideoxy-α-D-erythro-hex-2-enopyranosyl]-oxymethylcamptothecin Toluene sulfonic acid monohydrate (2.100 g) was placed in a 50 mL rounded bottomed flask and heated at reduced pressure until all of the solid was melted and the water removed. THF (10 mL), 7-hydroxymethyl camptothecin (0.700 g) and iodine (0.350 g) was added and pentaacetyl-(o-methoxy)benzoyl-lactal (3.500 g) in THF (10 mL) was added dropwise over the course of 2 h and the resultant reaction mixture was allowed to stir overnight. The reaction mixture was then poured into ethyl acetate (100 mL) and the organic layer was washed with saturated $Na_2S_2O_3$ (50 mL), saturated $NaHCO_3$ (50 mL), and brine (25 mL). The organic layer was then dried over $Na_2SO_4$, filtered, and concentrated and the resultant crude solid purified by silica gel chromatography (100% ethyl acetate) to give 7-[6-O-acetyl-4-O-(2,3,4,6-tetra-O-acetyl-β-D-galactopyranosyl)-2,3-dideoxy-α-D-erythro-hex-2-enopyranosyl]-hydroxymethylcamptothecin (1.190 g, 73%) as a pale yellow solid.

mp 143–146° C.; $[\alpha]_D^{20}$+44.5° (c=1.00, CHCl$_3$); $^1$H NMR (300 MHz, CDCl$_3$) δ1.030 (dd, J=7.2, 7.2 Hz, 3H), 1.912 (m, 2H), 1.978 (s, 6H), 2.061 (s, 3H), 2.118 (s, 3H), 2.166 (s, 3H), 4.006–4.329 (m, 7H), 4.638 (d, J=7.8 Hz, 1H), 5.018–5.498 (m, 8H), 5.740 (d, J=16.2, 1H), 5.882 (br d, J=10.3 Hz, 1H), 6.213 (d, J=10.3 Hz, 1H), 7.649 (dd, J=7.6, 7.6 Hz, 1H), 7.667 (s, 1H), 7.803 (dd, J=7.5, 7.5 Hz, 1H), 8.042 (d, J=7.5 Hz, 1H), 8.230 (d, J=7.5 Hz, 1H); $^{13}$C NMR (75 MHz, CDCl$_3$) δ7.83 (q), 20.50 (q, 2C), 20.61 (q, 2C), 20.81 (q), 31.81 (t), 50.43 (t), 61.31 (t), 62.87 (t), 65.05 (t), 66.37 (t), 66.99 (d), 68.25 (d), 68.99 (d), 70.74 (d), 70.84 (d), 72.76 (s), 73.03 (d), 94.35 (d), 97.84 (d), 101.89 (d), 118.75 (s), 123.34 (d), 126.00 (d), 127.33 (s), 128.02 (d), 130.14 (d), 130.55 (d), 131.68 (d), 132.58 (d), 138.26 (s), 146.25 (s), 148.99 (s), 149.96 (s), 152.54 (s), 157.45 (s), 169.15 (s), 169.82 (s), 170.02 (s, 2C), 170.35 (s, 2C), 173.70 (s); IR (KBr) 1053 (s), 1158 (m), 1228 (s), 1371 (m), 1438 (m), 1558 (w), 1614 (m), 1662 (m), 1751 (s), 3470 (w) cm$^{-1}$.

M) Synthesis Of 7-[4-O-(β-D-galactopyranosyl)-2,3-dideoxy-α-D-erythro-hex-2-enopyranosyl]-oxymethylcamptothecin 7-[6-O-acetyl-4-O-(2,3,4,6-tetra-O-acetyl-β-D-galactopyranosyl)-2,3-dideoxy-α-D-erythro-hex-2-enopyranosyl]-hydroxymethylcamptothecin (1.750 g) was placed in a 50 mL rounded bottom flask and 25 mL methanol was added. The mixture was then cooled to 0° C. and NH$_3$ was bubbled through (5.000 g dissolved) and the reaction mixture was allowed to stir overnight. The solvent was then removed under reduced pressure and the resultant crude purified by silica gel chromatography (50% methanol in ethyl acetate) to provide 7-[4-O-(β-D-galactopyranosyl)-2,3-dideoxy-α-D-erythro-hex-2-enopyranosyl]-hydroxymethylcamptothecin (0.976 g, 73%) as a light yellow solid.

mp 180–182° C.; $[\alpha]_D^{20}$+15.9° (c=1.00, DMF); $^1$H NMR (300 MHz, DMSO) δ0.894 (dd, J=7.3, 7.3 Hz, 3H), 1.881 (m, 2H), 3.259–3.629 (m, ), 4.080 (d, J=9.3 Hz, 1H, OH, 4.196 (br s, 1H, OH), 4.397 (d, J=4.5 Hz, 1H, OH), 4.571 (dd, J=5.5, 5.5 Hz, 1H, OH), 4.722 (m, 2H, OH), 4.932 (br s, 1H, OH), 5.240–5.436 (m, ), 5.788 (br d, J=10.5 Hz, 1H), 6.125 (d, J=10.5 Hz, 1H), 6.546 (s, 1H, OH), 7.345 (s, 1H), 7.741 (dd, J=7.5, 7.5 Hz, 1H), 7.875 (dd, J=7.5, 7.5 Hz, 1H), 8.175 (d, J=7.5 Hz, 1H), 8.273(d, J=7.5 Hz, 1H); $^{13}$C NMR (90 MHz, CDCl$_3$) δ7.69 (q), 30.23 (t), 50.11 (t), 60.20 (t), 60.37 (t), 64.07 (t), 65.18 (t), 68.11 (d), 70.49 (d), 71.12 (d), 71.56 (d), 72.29 (s), 73.24 (d), 75.13 (d), 93.17 (d), 96.56 (d), 104.69 (d), 119.00 (s), 124.41 (d), 125.39 (d), 125.99 (s), 127.71 (d), 128.29 (d), 129.57 (d), 130.05 (d), 133.64 (d), 138.86 (s), 145.39 (s), 148.10 (s), 149.88 (s), 152.38 (s), 156.68 (s), 172.37 (s); IR (KBr) 1054 (s), 1159 (w), 1232 (w), 1387 (w), 1512 (w), 1599 (s), 1658 (s), 1746 (m), 3394 (m) cm$^{-1}$.

N) Synthesis Of 7-[4,6-di-O-acetyl-2,3 dideoxy-α-D-erythro-hexanopyranosyl]-oxymethylcamptothecin 7-[4,6-di-O-acetyl-2,3 dideoxy-α-D-erythro-hex-2-enopyranosyl]-oxymethylcamptothecin (0.200 g) was added to p-toluenesulfonylhydrazine (0.960) and NaOAc (1.000 g) in 5 mL DMF and 3 mL water and warmed to reflux for 4 h. The reaction mixture was then allowed to cool, the solvent removed under reduced pressure and purification by silica gel chromatography (5% methanol in $CH_2Cl_2$) provided 7-[4,6-di-O-acetyl-2,3 dideoxy-α-D-erythro-hexanopyranosyl]-oxymethylcamptothecin as a light yellow solid (0.176 g, 88%).

mp 160–162° C.; $[\alpha]_D^{20}$+57.1° (c=1.00, $CHCl_3$); $^1H$ NMR (360 MHz, $CDCl_3$) δ1.043 (dd, J=7.2, 7.2 Hz, 3H), 1.928 (m, 4H), 2.047 (s, 3H), 2.063 (m, 2H), 2.141 (s, 3H), 3.860 (s, 1H, OH), 3.983 (m, 1H), 4.171 (1H) and 4.236 (1H) (AB q, $J_{AB}$=11.4 Hz, the 4.236 peaks are further split into d with J=5.2 Hz), 4.795 (m, 1H), 5.052 (s, 1H), 5.180, (d, J=14.1 Hz, 1H), 5.305 (d, J=16.2 Hz, 1H), 5.448 (m, 3H), 5.743 (d, J=14.1 Hz, 1H), 7.672 (s, 1H), 7.700 (dd, J=8.4, 7.6 Hz, 1H), 7.825 (dd, J=8.4, 7.6 Hz, 1H), 8.039 (d, J=8.4 Hz, 1H), 8.245 (d, J=7.6 Hz, 1H); $^{13}C$ NMR (90 MHz, $CDCl_3$) δ8.02 (q), 21.04 (q), 21.23 (q), 24.29 (t), 28.71 (t), 31.85 (t), 50.78 (t), 63.37 (t), 64.52 (t), 66.48 (t), 67.72 (d), 69.71 (d), 72.95 (s), 96.92 (d), 98.08 (d), 118.95 (s), 123.34 (d), 125.97 (s), 127.21 (s), 128.33 (d), 130.46 (d), 130.81 (d), 138.67 (s), 146.39 (s), 149.06 (s), 150.32 (s), 152.75 (s), 157.73 (s), 170.13 (s), 170.99 (s), 173.99 (s); IR (KBr) 1043 (m), 1155 (w), 1233 (s), 1368 (w), 1440 (w), 1457 (w), 1613 (m), 1661 (m), 1744 (s), 3471 (w) $cm^{-1}$.

O) Synthesis Of 7-[2,3-dideoxy-α-D-erythro-hexanopyranosyl]-oxymethylcamptothecin 7-[4,6-di-O-acetyl-2,3 dideoxy-α-D-erythro-hexanopyranosyl]-oxymethylcamptothecin (0.150 g) was placed in a 10 mL rounded bottom flash with 7.5 mL methanol and $NH_3$ bubbled through at 0° C. until 1 g added. The reaction mixture was then warmed to room temperature and allowed to stir overnight. The solvent was then removed under reduced pressure and the resultant crude solid purified by silica gel chromatography (5% methanol in ethyl acetate) to provide 7-[2,3-dideoxy-α-D-erythro-hexanopyranosyl]-oxymethylcamptothecin (0.077 g, 60%) as a light yellow solid.

Alternatively, 7-[2,3-dideoxy-α-D-erythro-hex-2-enopyranosyl]-oxymethylcamptothecin (0.023 g) was added to p-toluenesulfonylhydrazine (0.100) and NaOAc (0.096 g) in 2 mL DME and 1 mL water and warmed to reflux for 6 h. The reaction mixture was then allowed to cool, the solvent removed under reduced pressure and purification by silica gel chromatography (5% methanol in ethyl acetate) also provided 7-[2,3-dideoxy-α-D-erythro-hexanopyranosyl]-hydroxymethylcamptothecin (0.019 g, 83%) as a light yellow solid.

mp 235° C. (dec.); $[\alpha]_D^{20}$+36.3° (c=1.00, DMSO); $^1H$ NMR (300 MHz, DMSO) δ0.896 (dd, J=7.0, 7.0 Hz, 3H), 1.686–1.906 (m, 4H), 3.222–3.500 (m, 3H), 3.611 (m, 1H), 4.484 (dd, J=6.0, 5.2 Hz, 1H, OH), 4.791 (d, J=4.6 Hz, 1H, OH), 5.187 (1H) and 5.338 (1H) (AB q, $J_{AB}$=14.1 Hz), 5.367 (s, 2H), 5.431 (s, 2H), 6.538 (s, 1H), 7.342 (s, 1H), 7.729 (dd, J=8.2, 7.1 Hz, 1H), 7.871 (dd, J=8.2, 7.1 Hz, 1H), 8.181 (d, J=8.2 Hz, 1H), 8.209 (d, J=7.1 Hz, 1H); $^{13}C$ NMR (90 MHz, DMSO) δ7.71 (q), 20.69 (t), 27.28 (t), 28.69 (t), 50.35 (t), 61.05 (t), 63.11 (t), 64.79 (d), 65.18 (d), 72.31 (s), 75.17 (d), 95.55 (d), 96.50 (δ), 118.99 (s), 124.19 (d), 125.71 (s), 127.67 (d), 129.61 (d), 130.05 (d), 139.17 (s), 145.29 (s), 147.97 (s), 149.88 (s), 152.46 (s), 156.64 (s), 172.39 (s); IR (KBr) 1050 (s), 1398 (w), 1602 (s), 1659 (s), 1749 (m) 3385 (w) $cm^{-1}$.

P) Synthesis Of 7-[6-O-acetyl-4-O-(2,3,4,6-tetra-O-acetyl-α-D-glucopyranosyl)-2,3-dideoxy-α-D-erythro-hexanopyranosyl]-oxymethylcamptothecin 7-[6-O-acetyl-4-O-(2,3,4,6-tetra-O-acetyl-α-D-glucopyranosyl)-2,3-dideoxy-α-D-erythro-hex-2-enopyranosyl]-oxymethylcamptothecin (0.200 g) was added to a solution of p-toluenesulfonyl-hydrazine (0.400) and NaOAc (0.700 g) in 5 mL DME and 3 mL water and warmed to reflux for 6 h. The reaction mixture was then allowed to cool, poured into 50 mL ethyl acetate and washed successively with 50 mL water, 50 mL $NaHCO_3$, and 25 mL brine. The resultant organic layer was then dried ($Na_2SO_4$), filtered and the solvent removed under reduced pressure. Silica gel column chromatography (ethyl acetate) provided 7-[6-O-acetyl-4-O-(2,3,4,6-tetra-O-acetyl-α-D-glucopyranosyl)-2,3-dideoxy-α-D-erythro-hexanopyranosyl]-oxymethylcamptothecin (0.178 g, 89% as a light yellow powder.

mp 138–140° C.; $[\alpha]_D^{20}$+101.0° (c=1.00, $CHCl_3$); $^1H$ NMR (360 MHz, $CDCl_3$) δ1.044 (dd, J=7.3, 7.3 Hz, 3H), 1.258 (dd, J=7.9, 6.7 Hz, 1H), 1.775–2.087 (m, 5H), 1.993 (s, 3H), 2.023 (s, 3H), 2.062 (s, 3H), 2.105 (s, 3H), 2.198 (s, 3H), 3.676 (m, 1H), 3.836 (s, 1H), 3.966 (m, 2H), 4.102 (m, 1H), 4.305 (m, 3H), 4.826 (dd, J=10.4, 3.9 Hz, 1H), 4.997–5.488 (m, 9H), 5.719 (m, 1H), 7.680 (s, 1H), 7.701 (dd, J=7.5, 7.0 Hz, 1H), 7.847 (dd, J=8.2, 7.0 Hz, 1H), 8.100 (d, J=7.5 Hz, 1H), 8.270 (d, J=8.2 Hz, 1H); $^{13}C$ NMR (90 MHz, $CDCl_3$) δ8.03 (q), 20.89 (q, 4C), 21.12 (q), 23.65 (t), 28.56 (t), 31.83 (t), 50.59 (t), 61.84 (t), 63.87 (t), 63.94 (t), 66.54 (t), 68.38 (d, 2C), 69.93 (d, 2C), 70.72 (d), 71.89 (d), 72.96 (s), 93.28 (d), 96.36 (d), 98.08 (d), 118.90 (s), 123.56 (d), 126.27 (s), 127.54 (s), 128.39 (d), 130.53 (d), 130.86 (d), 138.43 (s), 146.53 (s), 149.25 (s), 150.22 (s), 152.79 (s), 157.70 (s), 169.73 (s), 170.23 (s), 170.45 (s), 170.80 (s), 170.91 (s), 174.09 (s); IR (KBr) 1038 (m), 1155 (w), 1229 (s), 1368 (w), 1615 (w), 1663 (w), 1749 (s), 3458 (w) $cm^{-1}$.

Q) Synthesis Of 7-[4-O-(α-D-glucopyranosyl)-2,3-dideoxy-α-D-erythro-hexanopyranosyl]-oxymethylcamptothecin 7-[6-O-acetyl-4-O-(2,3,4,6-tetra-O-acetyl-α-D-glucopyranosyl)-2,3-dideoxy-α-D-erythro-hexanopyranosyl]-oxymethylcamptothecin (0.100 g) was dissolved in 10 mL methanol and cooled to 0° C. and $NH_3$ bubbled through until 1.400 g was added. The resultant reaction mixture was then warmed to room temperature and allowed to stir for 16 h. The solvent was then removed under reduced pressure and the resultant crude solid purified by silica gel chromatography (25% methanol in ethyl acetate) to provide 7-[4-O-(α-D-glucopyranosyl)-2,3-dideoxy-α-D-erythro-hexanopyranosyl]-oxymethylcamptothecin (0.042 g, 55%) as a yellow solid.

Alternatively, 7-[6-O-acetyl-4-O-(2,3,4,6-tetra-O-acetyl-α-D-glucopyranosyl)-2,3-dideoxy-α-D-erythro-hexanopyranosyl]-oxymethylcamptothecin (0.100 g) was added to p-toluenesulfonyl-hydrazine (0.320) and NaOAc (0.390 g) in 5 mL DME and 3 mL water and warmed to reflux for 4 h. The reaction mixture was then allowed to cool to room temperature, 3 mL more water added and to solution cooled to 0° C. The precipitate was then removed by vacuum filtration, washed with water and $CHCl_3$, and pumped to dryness to again provide 7-[4-O-(α-D-glucopyranosyl)-2,3-dideoxy-α-D-erythro-hexanopyranosyl]-oxymethylcamptothecin (0.074 g, 73%) as a light yellow solid.

mp 225–228° C.; $[\alpha]_D^{20}$+89.4° (c=1.00, DMSO); $^1H$ NMR (360 MHz, DMSO) δ0.895 (dd, J=7.2, 7.2 Hz, 3H), 1.673 (m, 2H), 1.881 (m, 3H), 2.049 (m, 1H), 3.039 (m, 1H), 3.170 (m, 1H), 3.228–3.692 (m, 1OH), 4.490 (br s, 1H, OH), 4.63 (br s, 1H, OH), 4.624 (br s, 1H, OH), 4.831 (d, J=3.7 Hz, 1H), 4.832 (br s, 1H, OH), 5.034 (s, 1H, OH), 5.202 (d, J=14.3 Hz, 1H), 5.377 (m, 3H), 5.437 (s, 2H), 6.549 (s, 1H, OH), 7.347 (s, 1H), 7.744 (dd, J=8.3, 7.0 Hz, 1H), 7.881 (dd, J=7.2, 7.0 Hz, 1H), 8.195 (d, J=7.2 Hz, 1H), 8.228 (d, J=8.3 Hz, 1H); $^{13}$C NMR (90 MHz, DMSO) δ7.71 (q), 22.47 (t), 28.11 (t), 30.24 (t), 50.35 (t), 60.79 (t), 60.99 (t), 63.07 (t), 65.19 (t), 68.53 (d), 70.09 (d), 71.48 (d), 72.31 (s), 72.93 (d), 73.09 (d), 73.22 (d), 94.46 (d), 95.54 (d), 96.57 (d), 119.03 (s), 124.21 (d), 125.79 (s), 127.72 (d), 127.98 (s), 129.65 (d), 130.08 (d), 138.99 (s), 145.31 (s), 148.03 (s), 149.91 (s), 152.50 (s), 156.66 (s), 172.39 (s); IR (KBr) 1052 (s), 1602 (m), 1659 (m), 1746 (m), 3421 (s) cm$^{-1}$.

R) Synthesis Of 7-[6-O-acetyl-4-O-(2,3,4,6-tetra-O-acetyl-β-D-galactopyranosyl)-2,3-dideoxy-α-D-erythro-hexanopyranosyl]-oxymethylcamptothecin 7-[6-O-acetyl-4-O-(2,3,4,6-tetra-O-acetyl-β-D-galactopyranosyl)-2,3-dideoxy-α-D-erythro-hex-2-enopyranosyl]-oxymethylcamptothecin (0.200 g) was added to a solution of p-toluenesulfonyl-hydrazine (0.400) and NaOAc (0.700 g) in 5 mL DME and 3 mL water and warmed to reflux for 6 h. The reaction mixture was then allowed to cool, poured into 50 mL ethyl acetate and washed successively with 50 mL water, 50 mL NaHCO$_3$, and 25 mL brine. The resultant organic layer was then dried (Na$_2$SO$_4$), filtered and the solvent removed under reduced pressure. Silica gel column chromatography (ethyl acetate) provided 7-[6-O-acetyl-4-O-(2,3,4,6-tetra-O-acetyl-β-D-galactopyranosyl)-2,3-dideoxy-α-D-erythro-hexanopyranosyl]-oxymethylcamptothecin (0.175 g, 87% as a light yellow powder.

mp 148–150° C.; [α]$_D^{20}$+55.0° (c=1.00, CHCl$_3$); $^1$H NMR (300 MHz, CDCl$_3$) δ1.047 (dd, J=7.4, 7.4 Hz, 3H), 1.259 (dd, J=7.9, 6.7 Hz, 1H), 1.907 (m, 2H), 1.972 (s, 3H), 2.037 (s, 3H), 2.051 (s, 3H), 2.157 (s, 3H), 2.177 (s, 3H), 2.157 (s, 3H), 2.177 (s, 3H), 3.568 (m, 1H), 3.775 (s, 1H), 3.895 (m, 2H), 4.085 (m, 2H), 4.162 (m, 1H), 4.302 (br d, J=11.1 Hz, 1H), 4.549 (d, J=7.7 Hz), 4.981 (m, 2H), 5.148 (m, 2H), 5.408 (m, 5H), 5.759 (br d, J=6.6 Hz), 7.546 (dd, J=8.4, 6.6 Hz, 1H), 7.678 (s, 1H), 7.839 (dd, J=8.4, 6.6 Hz, 1H), 8.077 (d, J=8.4 Hz, 1H), 8.259 (d, J=8.4 Hz, 1H); $^{13}$C NMR (90 MHz, CDCl$_3$) δ8.05 (q), 20.86 (q, 4C), 21.15 (q), 26.47 (t), 28.96 (t), 31.86 (t), 50.67 (t), 61.38 (t), 63.69 (t), 64.07 (t), 66.61 (t), 67.01 (d), 69.02 (d), 70.16 (d), 70.79 (d), 71.10 (d), 72.96 (s), 76.50 (d), 96.44 (d), 98.09 (d), 102.41 (d), 118.92 (s), 123.58 (d), 126.20 (s), 127.46 (s), 128.40 (d), 130.52 (d), 130.87 (d), 138.53 (s), 146.54 (s), 149.23 (s), 150.22 (s), 152.81 (s), 157.79 (s), 169.73 (s), 170.34 (s), 170.58 (s), 170.97 (s), 174.16 (s); IR (KBr) 1074 (m), 1228 (s), 1369 (w), 1615 (m), 1662 (m), 1751 (s), 3473 (w) cm$^{-1}$.

S) Synthesis Of 7-[4-O-(β-D-galactopyranosyl)-2,3-dideoxy-α-D-erythro-hexanopyranosyl]-oxymethylcamptothecin 7-[6-O-acetyl-4-O-(2,3,4,6-tetra-O-acetyl-β-D-galactopyranosyl)-2,3-dideoxy-α-D-erythro-hexanopyranosyl]-oxymethylcamptothecin (0.100 g) was dissolved in 10 mL methanol, cooled to 0° C., and NH$_3$ bubbled through until 1.200 g were added. The reaction mixture was the warmed to room temperature and allowed to stir for 16 h. The solvent was then removed and the resultant crude solid purified by silica gel chromatography (25% methanol in ethyl acetate) to provide 7-[4-O-(β-D-galactopyranosyl)-2,3-dideoxy-α-D-erythro-hexanopyranosyl]-oxymethylcamptothecin 0.027 g, 36%) as a light yellow solid.

Alternatively, 7-[6-O-acetyl-4-O-(2,3,4,6-tetra-O-acetyl-β-D-galactopyranosyl)-2,3-dideoxy-α-D-erythro-hexanopyranosyl]-oxymethylcamptothecin (0.114 g) was added to p-toluenesulfonyl-hydrazine (0.320) and NaOAc (0.390 g) in 5 mL DME and 3 mL water and warmed to reflux for 4 h. The reaction mixture was then allowed to cool to room temperature, 3 mL more water added and to solution cooled to 0° C. The precipitate was then removed by vacuum filtration, washed with water and CHCl$_3$, and pumped to dryness to again provide 7-[4-O-(β-D-galactopyranosyl)-2,3-dideoxy-α-D-erythro-hexanopyranosyl]-oxymethylcamptothecin (0.072 g, 63%) as a light yellow solid.

mp 214–217° C.; [α]$_D^{20}$+37.4° (c=1.00, DMSO); $^1$H NMR (300 MHz, DMSO) δ0.869 (dd, J=7.3, 7.3 Hz, 3H), 1.744 (m, 2H), 1.868 (m, 3H), 2.004 (m, 1H), 3.230–3.639 (m, 1OH), 4.176 (d, J=5.5 Hz, 1H), 4.402 (br s, 1H, OH), 4.516 (br s, 1H, OH), 4.563 (br s, 1H, OH), 4.710 (m, 1H, OH), 4.926 (m, 1H, OH), 5.008 (s, 1H), 5.225 (1H) and 5.345 (1H) (AB q, J$_{AB}$=13.7 Hz), 5.403 (s, 2H), 5.440 (s, 2H), 6.550 (s, 1H, OH), 7.350 (s, 1H), 7.761 (dd, J=8.1, 6.7 Hz), 7.891 (dd, J=8.4, 6.7 Hz, 1H), 8.205 (d, J=8.4 Hz, 1H), 8.247 (d, J=8.1 Hz, 1H); $^{13}$C NMR (90 MHz, DMSO) δ7.70 (q), 26.22 (t), 28.62 (t), 30.22 (t), 50.29 (t), 60.30 (t), 60.68 (t), 63.26 (t), 65.18 (t), 67.95 (d), 70.67 (d), 72.30 (s), 73.18 (d), 73.34 (d), 74.52 (d), 75.07 (d), 95.65 (d), 96.55 (d), 104.53 (d), 119.02 (s), 124.19 (d), 125.76 (s), 127.70 (d), 127.91 (s), 129.63 (d), 130.07 (d), 138.99 (s), 145.29 (s), 147.99 (s), 149.88 (s), 152.46 (s), 156.65 (s), 172.40(s); IR (KBr) 1031 (s), 1606 (s), 1659 (s), 1749 (s), 3450 (s) cm$^{-1}$.

T) Synthesis Of Camptothecin 20-n-Hexanoate

Camptothecin (0.700 g) and n-hexanoyl chloride (2.20 mL) were dissolved in 110 mL of a 2:1 mixture of DMF and pyridine and the solution was heated at 80° C. for 6 hours. The reaction mixture was then poured into 200 mL of CH$_2$Cl$_2$ and the resulting mixture was washed successively with water (2×200 mL), 200 mL of 5% aqueous HCl, and 100 mL of brine. The organic layer was dried over anhydrous Na$_2$SO$_4$ and concentrated under reduced pressure. The crude solid thus obtained was purified by silica gel flash chromatography with ethyl acetate as the eluent to give camptothecin 20-n-hexanoate (0.502 g, 56%) as a light yellow solid: mp 250–252° C.; [α]$_D^{20}$–56.0° (c=1.00, CHCl$_3$); $^1$H NMR (300 MHz, CDCl$_3$) δ0.854 (diffused t, 3H, J=7.6 Hz), 0.978 (t, 3H, J=7.5 Hz), 1.25–1.40 (m, 4H), 1.60–1.72 (m, 2H), 2.17 (1H) and 2.31 (1H) (ABq, J$_{AB}$=13.8 Hz; both the 2.17 and 2.31 peaks are further split into q with J=7.6 and 7.7 Hz, respectively), 2.48 (1H) and 2.49 (1H) (ABq, J$_{AB}$=14.6 Hz; both the 2.48 and 2.49 peaks are further split into t with J=7.3 and 7.6 Hz, respectively), 5.29 (s, 2H), 5.42 (1H), 5.68 (1H), (ABq, J$_{AB}$=14.3 Hz), 7.22 (s, 1H), 7.67 (ddd, 1H, J=8.1, 6.9, 1.2 Hz, 1H), 7.84 (ddd, 1H, J=8.5, 6.9, 1.5 Hz), 7.94 (dd, J=8.1, 1.5 Hz, 1H), 8.21 (dd, J=8.5, 1.2 Hz, 1H), 8.40 (s, 1H); $^{13}$C NMR (90 MHz, CHCl$_3$) δ7.75 (q), 14.04 (q), 22.48 (t), 24.50 (t), 31.32 (t), 32.04 (t), 33.96 (t), 50.07 (t), 67.28 (t), 75.82 (s), 96.18 (d), 120.50 (s), 128.19 (d), 128.35 (s), 128.40 (d), 128.64 (s), 129.76 (d), 130.84 (d), 131.36 (d), 146.17 (s), 146.37 (s), 149.04 (s), 152.57 (s), 157.54 (s), 167.78 (s), 172.98(s); IR (KBr) 722 (w), 756 (w), 1043 (w), 1229 (w), 1404 (m), 1627 (m), 1673 (m), 1743 (s), 1758 (s) cm$^{-1}$.

EXAMPLE 4

Synthesis Of Novel Glycosylated Hexacyclic Camptothecin Analogs

In their 1994 paper, Sugimori et al described the synthesis of novel hexacyclic camptothecin compounds. [See Sugimori et al. "Antitumor Agents. Synthesis And Antitumor Activity Of Novel Hexacyclic Camptothecin Analogues," J. Med. Chem. 37:3033 (1994)]. Sugimori and coworkers were able to synthesize the novel hexacyclic camptothecin compounds which have an additional 5-, 6-, or 7-membered ring cyclized at positions 7 and 9 of camptothecin by intramolecular cyclization of pentacyclic camptothecin compounds or Friedlander condensation of the appropriate bicyclic amino ketone and tricyclic ketone. All of the hexacyclic camptothecin compounds synthesized had comparable in vitro activity compared to SN-38 (the active metabolite of CPT-11), and some even had superior in vivo anti-cancer activity. However, none were glycosylated by Sugimori and coworkers.

The present invention contemplates preparation of a novel glycosylated hexacyclic camptothecin analog by reaction of a hexacyclic camptothecin compound with one or more appropriate alkylhydroxyl linkers to form a hexacyclic camptothecin analog possessing free hydroxyl groups, followed by glycosylation as described above to form the novel glycosylated hexacyclic camptothecin analog. A representative contemplated novel glycosylated hexacyclic camptothecin analog is illustrated in FIG. 20.

From the above, it should be evident that the analogs of the present invention provide a powerful anticancer therapeutic agent. In side by side in vivo studies, novel compounds of the present invention were found to be superior to existing derivatives in both continuous and single dose treatment protocols.

We claim:

1. A method of synthesizing a disaccharide glycal, comprising the steps:
    a) providing in any order: i) unmodified disaccharide; ii) a protecting reagent; iii) a disaccharide derivatizing reagent; and iv) a reducing agent;
    b) reacting said unmodified disaccharide with said protecting reagent to form a protected disaccharide;
    c) reacting said protected disaccharide of step (b) with said disaccharide derivatizing reagent to form a disaccharide halide; and
    d) reacting said disaccharide halide of step (c) with said reducing agent to form a disaccharide glycal.

2. The method of claim 1, wherein said unmodified disaccharide is selected from the group consisting of maltose and lactose.

3. The method of claim 1, wherein said protecting reagent is an esterifying reagent.

4. The method of claim 3, wherein said esterifying reagent is acetic anhydride.

5. The method of claim 1, wherein said disaccharide derivatizing reagent is a halogenating reagent.

6. The method of claim 5, wherein said halogenating reagent is hydrobromic acid.

7. The method of claim 1, wherein said reducing reagent is zinc/cuprous sulfate.

8. A method of synthesizing an activated disaccharide glycal, comprising the steps:

a) providing in any order:
    i) disaccharide glycal,
    ii) an activating reagent, and
    iii) a catalyst;
b) reacting in any order:
    i) said disaccharide glycal,
    ii) said activating reagent, and
    iii) said catalyst to form an activated disaccharide glycal.

9. The method of claim 8, wherein said disaccharide glycal is maltose glycal.

10. The method of claim 8, wherein said activating reagent is a carboxylic acid.

11. The method of claim 10, wherein said carboxylic acid is o-anisic acid.

12. The method of claim 8, wherein said catalyst is a molecular diatomic halogen.

13. The method of claim 12, wherein said molecular diatomic halogen is molecular diatomic iodine.

14. The method of claim 8, wherein said activated disaccharide glycal is pentaacetylbenzoyl maltal.

15. A method of synthesizing a chemotherapeutic anti-cancer glycosylated analog of camptothecin of structure:

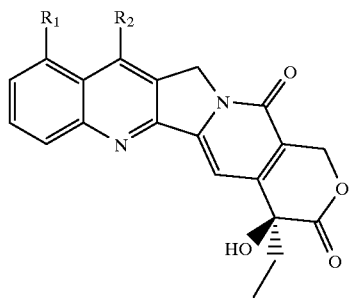

wherein $R_1$ is H and $R_2$ is $CH_2OR_3$; $R_3$ is glycosyl; or $R_1$ and $R_2$ together are a heterocyclic ring, said heterocyclic ring comprises a glycosyl group, comprising the steps:
    a) providing: i) a modified camptothecin; and ii) a catalyst;
    b) synthesizing a disaccharide glycal;
    c) treating said disaccharide glycal so as to generate an activated disaccharide glycal; and
    d) reacting in any order: i) said modified camptothecin of step (a); ii) said activated disaccharide glycal of step (c); and iii) said catalyst, under conditions as to form a chemotherapeutic anti-cancer glycosylated analog of camptothecin.

16. The method of claim 15, wherein the modified camptothecin of step (a) is prepared by reacting unmodified camptothecin with methanol and molecular diatomic iodine to form a modified camptothecin.

17. The method of claim 15, wherein the disaccharide glycal of step (b) is synthesized according to the following procedure:
    1) providing in any order:
        i) unmodified disaccharide,
        ii) acetic anhydride,
        iii) hydrobromic acid, and
        iv) zinc/cuprous sulfate;
    2) reacting said unmodified disaccharide with said acetic anhydride to form a protected disaccharide;
    3) reacting said protected disaccharide of step (2) with said hydrobromic acid to form a derivatized protected disaccharide; and 4) reacting said derivatized protected disaccharide of step (3) with said zinc/cuprous sulfate to form a disaccharide glycal.

18. The method of claim 17, wherein the treating in step (c) comprises reacting in any order:
   i) said disaccharide glycal,
   ii) o-anisic acid, and
   iii) molecular diatomic iodine to form an activated disaccharide glycal.

19. The method of claim 15, wherein said catalyst is a molecular diatomic halogen.

20. The method of claim 19, wherein said molecular diatomic halogen is molecular diatomic iodine.

21. A method of synthesizing a chemotherapeutic anti-cancer glycosylated analog of camptothecin of the structure:

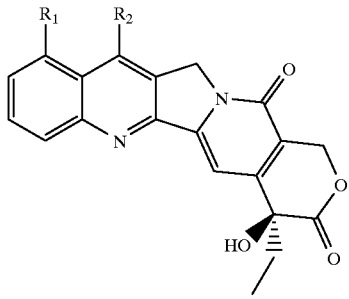

wherein $R_1$ is H and $R_2$ is $CH_2OR_3$; $R_3$ is glycosyl; or $R_1$ and $R_2$ together are a heterocyclic ring, said heterocyclic ring comprises a glycosyl group, comprising the steps:

a) providing in any order:
   i) unmodified camptothecin,
   ii) one or more modifying reagents,
   iii) a carbohydrate glycal, and
   iv) a catalyst;

b) reacting said unmodified camptothecin with said one or more modifying reagents to form a modified camptothecin having an additional hydroxyl group; and c) reacting in any order:
   i) said modified camptothecin of step (b),
   ii) said carbohydrate glycal, and
   iii) said catalyst to form a chemotherapeutic anti-cancer glycosylated analog of camptothecin.

22. The method of claim 21, wherein said one or more modifying reagents comprise methanol.

23. The method of claim 21, wherein said carbohydrate glycal is selected from the group consisting of glucose glycal, maltose glycal, and lactose glycal.

24. The method of claim 21, wherein said catalyst is a molecular diatomic halogen.

25. The method of claim 24, wherein said molecular diatomic halogen is molecular diatomic iodine.

* * * * *

UNITED STATES PATENT AND TRADEMARK OFFICE
CERTIFICATE OF CORRECTION

PATENT NO. : 5,932,709
DATED : 08/03/99
INVENTOR(S) : Brian Keith Shull et al.

It is certified that error appears in the above-identified patent and that said Letters Patent is hereby corrected as shown below:

In column 25, line 6, please delete "OH" and insert --O$\underline{H}$--.

In column 25, line 9, please delete "OH" and insert --O$\underline{H}$--.

In column 27, line 4, please delete "(m, 1 H, OH), 4.741 (m, 3H, OH0, 4.858 (br s, 1H, OH)" and insert --(m, 1 H, O$\underline{H}$), 4.741 (m, 3H, O$\underline{H}$), 4.858 (br s, 1H, O$\underline{H}$)--.

In column 27, line 9, please delete "OH" and insert --O$\underline{H}$--.

In column 28, line 48, please delete "OH" and insert --O$\underline{H}$--.

In column 28, line 49, please delete "4.196 (br s, 1H, OH), 4.397 (d, J=4.5 Hz, 1H, OH), 4.571" and insert --4.196 (br s, 1H, O$\underline{H}$), 4.397 (d, J=4.5 Hz, 1H, O$\underline{H}$), 4.571--.

In column 28, line 50, please delete "(dd, j=5.5, 5.5 Hz, 1H, OH), 4.722 (m, 2H, OH), 4.932" and insert --(dd, j=5.5, 5.5 Hz, 1H, O$\underline{H}$), 4.722 (m, 2H, O$\underline{H}$), 4.932--.

In column 28, line 51, please delete "OH" and insert --O$\underline{H}$--.

In column 28, line 52, please delete "OH" and insert --O$\underline{H}$--.

In column 29, line 13, please delete "OH" and insert --O$\underline{H}$--.

In column 29, line 56, please delete "OH" and insert --O$\underline{H}$--.

In column 29, line 57, please delete "OH" and insert --O$\underline{H}$--.

In column 31, line 2, please delete "(m, 1OH), 4.490 (br s, 1H, OH)" and insert --(m, 1OH), 4.490 (br s, 1H, O$\underline{H}$)--.

UNITED STATES PATENT AND TRADEMARK OFFICE
CERTIFICATE OF CORRECTION

PATENT NO. : 5,932,709
DATED : 08/03/99
INVENTOR(S) : Brian Keith Shull et al.

It is certified that error appears in the above-identified patent and that said Letters Patent is hereby corrected as shown below:

In column 31, line 3, please delete "4.63 (br s, 1H, OH), 4.624 (br s, 1H, OH)" and insert --4.63 (br s, 1H, O$\underline{H}$), 4.624 (br s, 1H, O$\underline{H}$)--.

In column 31, line 4, plese delete "(br s 1H, OH), 5.034 (s, 1H, OH)" and insert --(brs, 1H, O$\underline{H}$), 5.034 (s, 1H, O$\underline{H}$)--.

In column 31, line 6, please delete "OH" and insert --O$\underline{H}$--.

In column 32, line 22, please delete "(m, 10H), 4.176 (d, J=5.5 Hz, 1H), 4.402 (br s, 1H, OH)" and insert --(m, 10H), 4.176 (d, J=5.5 Hz, 1H), 4.402 (br s, 1H, O$\underline{H}$)--.

In column 32, line 23, please delete "OH), 4.563 ( br s 1H, OH)" and insert --O$\underline{H}$), 4.563 (brs, 1H, O$\underline{H}$)--.

In column 32, line 24, please delete "OH), 4.926 (m, 1H, OH)" and insert --O$\underline{H}$), 4.926 (m, 1H, O$\underline{H}$)--.

In column 32, line 26, please delete "OH" and insert --O$\underline{H}$--.

Signed and Sealed this

Twenty-seventh Day of June, 2000

Attest:

Q. TODD DICKINSON

Attesting Officer

Director of Patents and Trademarks